(12) United States Patent
Al-Mardeai et al.

(10) Patent No.: US 12,195,707 B2
(45) Date of Patent: *Jan. 14, 2025

(54) SIMULTANEOUS ENZYMATIC CELLULOSE HYDROLYSIS AND PRODUCT SEPARATION IN A RADIAL-FLOW MEMBRANE BIOREACTOR

(71) Applicant: UNITED ARAB EMIRATES UNIVERSITY, Al Ain (AE)

(72) Inventors: Saleha Al-Mardeai, Al Ain (AE); Sulaiman Al-Zuhair, Al Ain (AE); Bart Van Der Bruggen, Al Ain (AE); Emad Elnajjar, Al Ain (AE); Boguslaw Kruczek, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

This patent is subject to a terminal disclaimer.

(21) Appl. No.: 17/960,099

(22) Filed: Oct. 4, 2022

(65) Prior Publication Data

US 2023/0265374 A1 Aug. 24, 2023

Related U.S. Application Data

(63) Continuation-in-part of application No. 17/676,099, filed on Feb. 18, 2022, now Pat. No. 11,499,132.

(51) Int. Cl.
| | | |
|---|---|---|
| *C12N 9/24* | (2006.01) | |
| *C12M 1/00* | (2006.01) | |
| *C12M 1/12* | (2006.01) | |
| *C12M 1/40* | (2006.01) | |
| *C12N 9/42* | (2006.01) | |
| *C12P 7/10* | (2006.01) | |
| *C13K 1/04* | (2006.01) | |

(52) U.S. Cl.
CPC ............ *C12M 21/18* (2013.01); *C12M 29/04* (2013.01); *C12N 9/2437* (2013.01); *C12P 7/10* (2013.01); *C13K 1/04* (2013.01)

(58) Field of Classification Search
CPC . C12N 9/42; C12M 1/00; C12M 1/26; C12M 1/06; C12M 1/02; C12P 19/02; C12P 19/14
See application file for complete search history.

(56) References Cited

U.S. PATENT DOCUMENTS

| | | |
|---|---|---|
| 5,637,502 A | 6/1997 | Scott et al. |
| 5,705,390 A | 1/1998 | Kadouri et al. |
| 7,198,941 B2 | 4/2007 | Fadnavis et al. |
| 8,435,781 B2 | 5/2013 | Kodama |

FOREIGN PATENT DOCUMENTS

| | | |
|---|---|---|
| CN | 203807228 U | 9/2014 |
| CN | 204490595 U | 7/2015 |
| CN | 106830302 A | 6/2017 |
| CN | 207581458 U | 7/2018 |
| CN | 210795919 U | 6/2020 |
| GN | 102716669 A | 10/2012 |

OTHER PUBLICATIONS

Al-Mardeai, Saleha, et al. "Simultaneous Enzymatic Cellulose Hydrolysis and Product Separation in a Radial-Flow Membrane Bioreactor." Molecules 27.1 (2022): 288.
Al-Mardeai, Saleha, et al. "Dynamic model of simultaneous enzymatic cellulose hydrolysis and product separation in a membrane bioreactor." Biochemical Engineering Journal 174 (2021): 108107.
Dubey, Alka, et al. "Potential of membrane bioreactors' in ethanol and biogas production a review." Int J Chem Chem Eng 3.3 (2013): 131-138.

*Primary Examiner* — Maryam Monshipouri
(74) *Attorney, Agent, or Firm* — Nath, Goldberg & Meyer; Joshua B. Goldberg

(57) ABSTRACT

The membrane bioreactor for simultaneous enzymatic cellulose hydrolysis and product separation is a vessel having a lower hydrolysis reaction chamber and an upper distilled water chamber separated by a semipermeable membrane attached to the top of the lower reaction chamber. The membrane is supported on a stainless steel mesh and sealed to the mesh by epoxy glue to prevent leakage. A peristaltic pump is connected to the reaction chamber and maintains a flow of distilled water through the membrane and the upper chamber, the effluent being collected in a beaker or other product collection vessel. The reaction chamber is agitated at a moderate rate by a magnetic stirrer, and the upper chamber is agitated more rigorously by a mechanical stirrer. A thermocouple and temperature controller and a buffer solution, respectively, maintain temperature and pH in the reaction chamber optimal for enzymatic hydrolysis of cellulose.

20 Claims, 16 Drawing Sheets

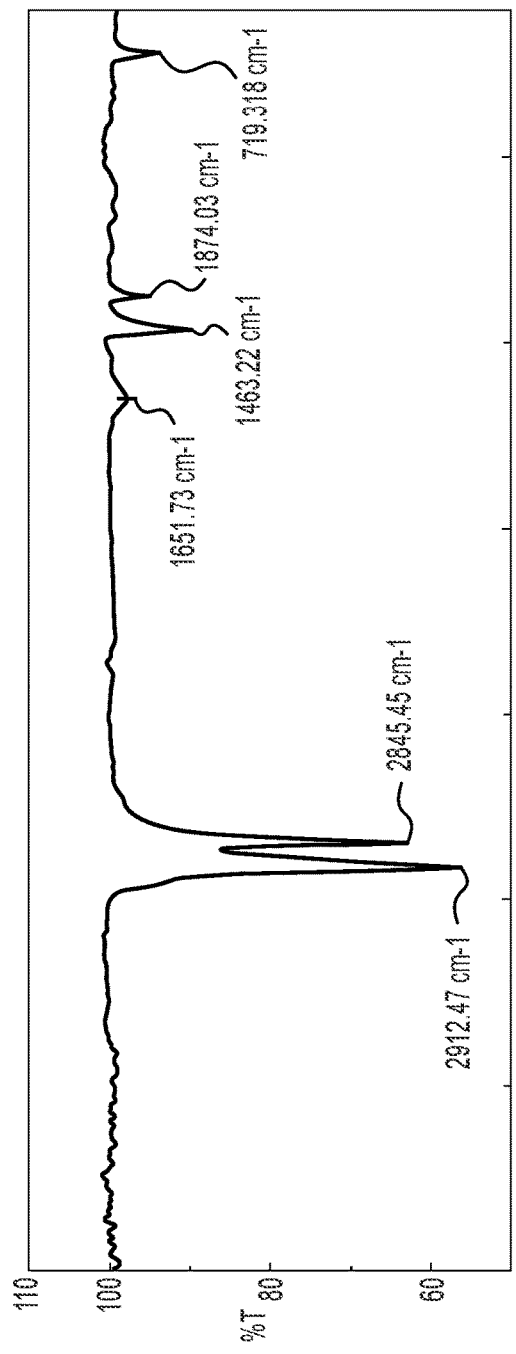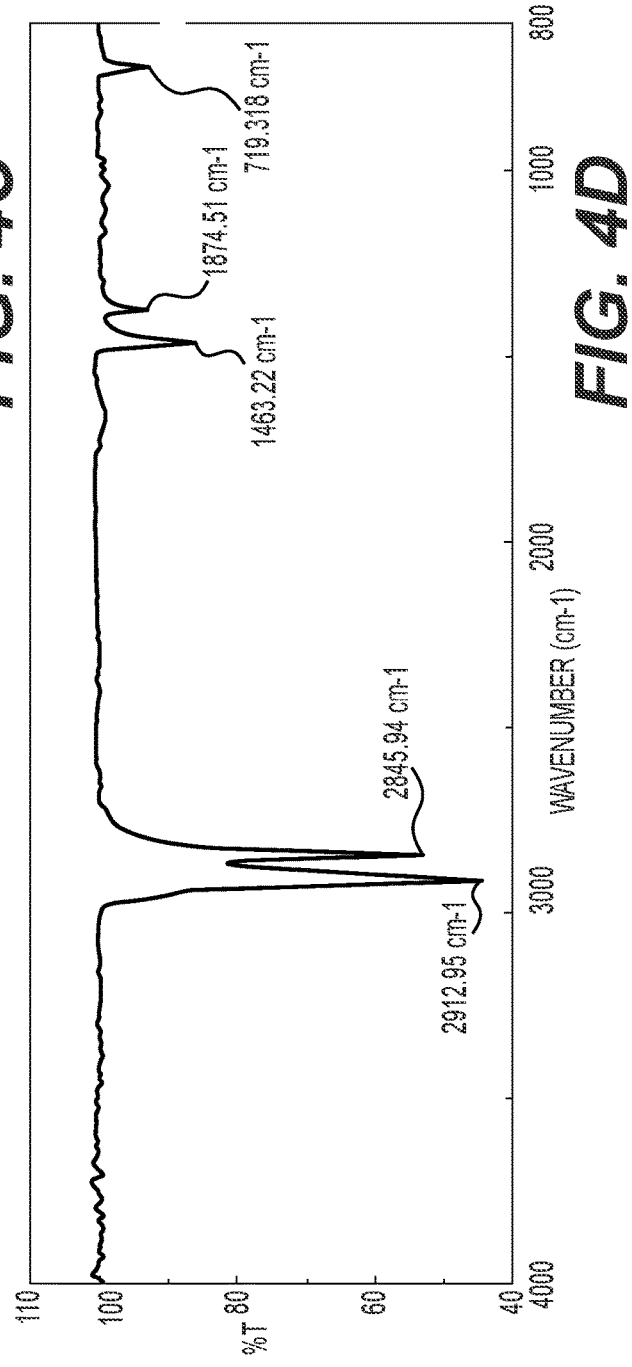

SIMULTANEOUS ENZYMATIC CELLULOSE HYDROLYSIS AND PRODUCT SEPARATION IN A RADIAL-FLOW MEMBRANE BIOREACTOR

CROSS-REFERENCE TO RELATED APPLICATION

This application is a continuation-in-part of U.S. patent application Ser. No. 17/676,099, filed on Feb. 18, 2022.

BACKGROUND

1. Field

The disclosure of the present patent application relates to extracting sugars from biomass, and particularly to a membrane bioreactor for simultaneous enzymatic cellulose hydrolysis and product separation to provide glucose that may be used, e.g., in the production of bioethanol.

2. Description of the Related Art

Recent decades have seen tremendous growth in the potential development of biofuels as an alternative to fossil fuels in order to improve environmental air quality and as a possible means to slow climate change resulting from fossil fuel emissions from power plants and modern modes of transportation. One of these biofuels is bioethanol. As a fuel, ethanol has a high octane rating. The combustion of ethanol produces carbon dioxide and water. It does not produce carbon monoxide, nitrates, sulfates, or other toxic emissions or pollutants. Moreover, when mixed or blended with gasoline, it oxidizes the fossil fuel, leading to more complete combustion of gasoline and reducing dependence on fossil fuel. Although ethanol may be produced by synthesis from fossil fuels, it may also be produced from biomass, thereby at least partially offsetting the production of carbon dioxide by consumption of carbon dioxide in the process of growing the plant material from which ethanol can be produced.

Currently, most bioethanol is made from corn, sugar cane, sugar beets, and other crops that are high in starch or simple sugar content. Such crops may be easily hydrolyzed by strong or dilute acids to produce glucose or other simple sugars, such as fructose, which are then converted to ethanol by fermentation. There is some concern, however, that use of arable lands for growth of these crops to produce ethanol may result in competition with food crops that will cause a rise in food prices and therefore be economically infeasible.

For that reason, there has been interest in and research directed towards the use of waste biomass to produce ethanol. Waste biomass is largely composed of lignocellulose. Starch and cellulose are both polymers containing long chains of glucose molecules. However, while starch is readily broken down to glucose molecules that can be converted to ethanol by fermentation, waste biomass includes lignin molecules linking the glucose chains, rendering the cellulose a more complex structure than starch, more woody and fibrous, and hence less susceptible to hydrolysis. The most economical and efficient way to hydrolyze lignocellulose may be by enzymatic catalysts and semipermeable membranes. However, such methods are currently not used commercially. Enzymes that are capable of breaking down and hydrolyzing lignocellulose to produce glucose are expensive. It will probably require a method that permits recycling and reuse of the enzyme catalyst, preferably in a single stage. Current progress has advanced only so far as a two stage method in which the hydrolysis mixture is removed from the reaction chamber and separated in a chamber having a semipermeable membrane, and returning any unreacted lignocellulose and enzyme catalyst to the reaction chamber, which results in a higher concentration of the hydrolysis-resistant reactant, making it difficult to mix and resulting in fouling and caking on the membrane; or single-stage methods using reactors subject to more frequent fouling of the membrane due to the position of the membrane in the reactor.

Thus, a membrane bioreactor for simultaneous enzymatic cellulose hydrolysis and product separation solving the aforementioned problems is desired.

SUMMARY

The membrane bioreactor for simultaneous enzymatic cellulose hydrolysis and product separation is a vessel having a lower hydrolysis reaction chamber and an upper distilled water chamber separated by a semipermeable membrane attached to the top of the lower reaction chamber. The membrane is supported on a stainless steel mesh and sealed to the mesh by epoxy glue to prevent leakage. A peristaltic pump is connected to the reaction chamber and maintains a flow of distilled water through the membrane and the upper chamber, the effluent being collected in a beaker or other product collection vessel. The reaction chamber is agitated at a moderate rate by a magnetic stirrer, and the upper chamber is agitated more rigorously by a mechanical stirrer. A thermocouple and temperature controller and a buffer solution, respectively, maintain temperature and pH in the reaction chamber optimal for enzymatic hydrolysis of cellulose.

In an alternative embodiment, the membrane bioreactor for simultaneous enzymatic cellulose hydrolysis and product separation is configured as a radial-flow membrane bioreactor for enzymatic cellulose hydrolysis and product separation. The radial-flow membrane bioreactor for enzymatic cellulose hydrolysis and product separation is a bioreactor for producing a biofuel intermediate, such as glucose, through bacterial-based enzymatic hydrolysis of a cellulose biomass. The produced glucose can then be converted into the biofuel ethanol, for example. The radial-flow membrane bioreactor includes a hollow housing having a lower wall, an upper wall and a cylindrical sidewall. The cylindrical sidewall has an outlet port mounted therein, and the upper wall has an inlet port mounted therein. A cylindrical filter is mounted coaxially within the hollow housing and extends between the lower wall and the upper wall. The cylindrical filter is formed from a semipermeable polyethersulfone membrane.

In use, water may be delivered into a reaction region defined by the cylindrical filter by a conduit extending through the inlet port, extending from outside the hollow housing into the reaction region. The cellulose biomass and the cellulase enzyme for performing enzymatic hydrolysis on the cellulose are placed within the reaction region inside the cylindrical filter and adjusted to pH 5 by a pH buffer in distilled water. Fresh distilled water with pH adjusted to pH 5 is placed in the cylindrical annulus between the cylindrical filter and the outer cylindrical housing sidewall. The biofuel intermediate (aqueous glucose) produced by the enzymatic hydrolysis process mixes with the water in the inner reaction region, and this filtrate flows radially through the cylindrical filter, which filters any additional reaction products and/or remnants of the reactants. The outlet port releases the aqueous glucose product, where the product glucose may be separated out from the water.

Within the reaction region, the mixture may be stirred by any suitable type of stirrer or mixer. For example, a magnetic stirrer may be used. The mixture and the reactants may also be heated within the reaction region by any suitable type of heater. For example, the radial-flow membrane bioreactor may be placed on top of a hot plate.

These and other features of the present subject matter will become readily apparent upon further review of the following specification.

BRIEF DESCRIPTION OF THE DRAWINGS

FIGS. 4C and 4D are FTIR spectra of a PES-30 membrane before (FIG. 4C) and after (FIG. 4D) use of the membranes in the membrane bioreactor of FIG. 1 for enzymatic hydrolysis of cellulose.

Similar reference characters denote corresponding features consistently throughout the attached drawings.

DETAILED DESCRIPTION OF THE PREFERRED EMBODIMENTS

The membrane bioreactor for simultaneous enzymatic cellulose hydrolysis and product separation is a vessel having a lower hydrolysis reaction chamber and an upper distilled water chamber separated by a semipermeable membrane attached to the top of the lower reaction chamber. The membrane is supported on a stainless-steel mesh and sealed to the mesh by epoxy glue to prevent leakage. A peristaltic pump is connected to the reaction chamber and maintains a flow of distilled water through the membrane and the upper chamber, the effluent being collected in a beaker or other product collection vessel. The reaction chamber is agitated at a moderate rate by a magnetic stirrer, and the upper chamber is agitated more rigorously by a mechanical stirrer. A thermocouple and temperature controller and a buffer solution may be used to maintain temperature and pH in the reaction chamber optimal for enzymatic hydrolysis of cellulose.

The structure and operation of the membrane bioreactor will be better understood by reference to the following examples of a prototype membrane bioreactor and experiments to test the effectiveness of the prototype.

Materials used in the experiments included the following. Cellulase produced by *Trichoderma reesei* was purchased from Merck, USA. Dinitrosalicylic acid (DNS), glucose (99.5% purity), Bradford reagent for protein detection, and all other chemicals were purchased from Merck, USA. Whatman quantitative filter paper (Grade 40) was shredded to be used as a standard cellulose substrate, with dimensions of 5×5 mm. Sodium acetate (99%) and acetic acid (99%) were used to prepare a 0.1 M acetate buffer (pH, 5) for controlling the pH of the system at 4.8. Microdyn Nadir hydrophilic polyethersulfone (PES) ultrafiltration membranes (297×210 mm) with MWCO values of 10, 30, and 50 kDa and a thickness of 230 μm were used.

Figure 1:
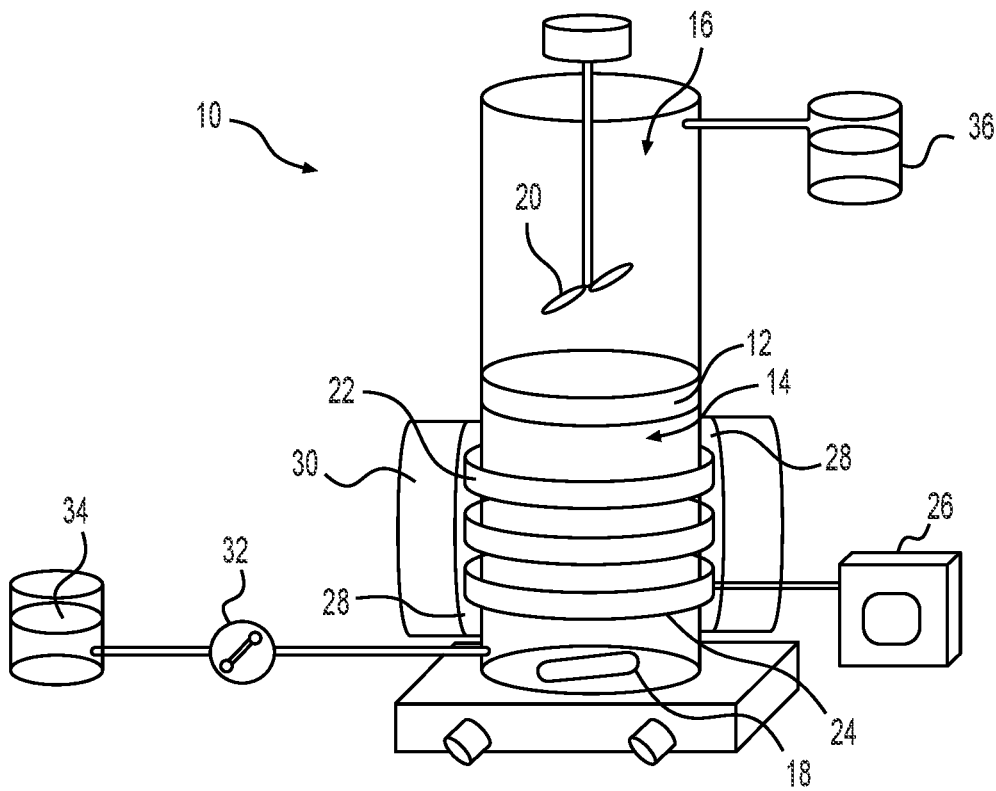
FIG. 1 is schematic diagram of an exemplary membrane bioreactor for simultaneous enzymatic cellulose hydrolysis and product separation.
Figure 2:
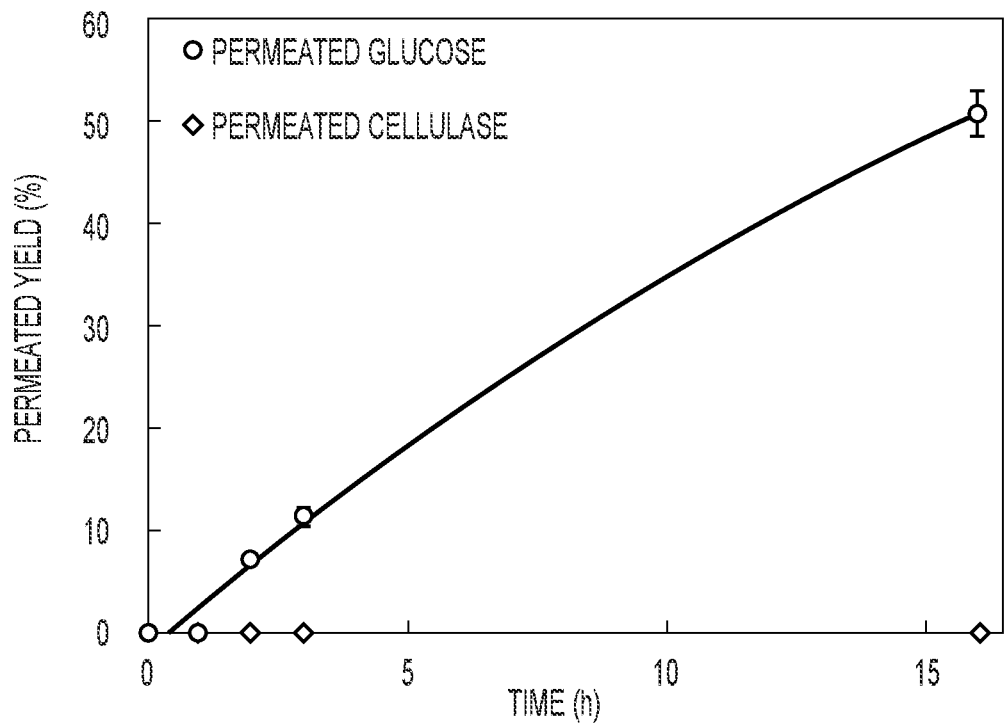
FIG. 2 is a composite plot comparing percent permeation of glucose with percent permeation of the enzyme catalyst cellulase through the semipermeable membrane of the membrane bioreactor of FIG. 1 as a function of time.

The membrane bioreactor (MBR) 10 is designed and built to comprise two zones, each having an internal diameter (ID) of 75 mm and height, h, of 150 mm, separated by a PES membrane 12, as shown in FIG. 1. The reaction cell or chamber 14 is the bottom or lower chamber, in which the substrate and enzyme are charged, and the reaction occurs. This design, which is opposite to the conventional dead-end filtration concept in which the membrane is positioned on the bottom of the reaction chamber, decreases substrate accumulation on the membrane surface and internal fouling. Previous methods of enzymatic cellulose hydrolysis with simultaneous product separation, a dead-end MBR, in which the membrane was placed at the bottom of the reaction cell, or in a separate unit adapting dead-end filtration concept, leads to substrate deposition due to gravity, resulting in the formation of a filter cake on the membrane. To minimize this effect, the membrane 12 is placed on top of the reaction cell 14, which is in contrast to the dead-end filtration concept. This approach rendered the gravity effect favorable and decreased substrate accumulation on the membrane surface, and together with the height of the reaction cell 14 of the MBR 10, settling of the substrate particles before reaching the membrane surface was possible. The PES membrane 12 was secured on the top of the reaction cell 14 by tightly gluing its perimeter to a woven stainless steel wire mesh that provided physical support during the diffusion process. To avoid leakage, the attached membrane 12 on the mesh was sealed with epoxy adhesive glue.

The produced glucose molecule permeates the semipermeable membrane 12 and move to the upper zone or distilled water chamber 16 that contained only distilled water. Both zones are agitated at a speed sufficient to create turbulence for good mixing, while avoiding excessive shear stress that can denature the enzyme. Agitation of the lower part of the reaction cell 14, which is another modification not used in previous designs, creates turbulence for mixing and at the same time contributes to reduction of the internal fouling and filter cake formation on the membrane 12. This positive effect of tangential forces, caused by mixing, reduces fouling on membrane surfaces, and therefore, filter cake deposition is not encountered. While the agitation speed in the reaction cell 14 was enough to create turbulence, it is kept low to avoid harsh shear stresses that might denature the enzymes. The latter is not a concern in the upper cell 16. Therefore, the reaction cell 14 is agitated with a magnetic stirrer bar 18 at 450 rpm, whereas the upper zone 16 is agitated using a mechanical stirrer 20 (IKA-WERK, Germany) with a higher speed of 1000 rpm to provide efficient distribution of the diffused glucose. Membrane damage is not encountered, since agitation was parallel to the membrane 12. The temperature of the reaction was maintained at 48° C. by covering the bottom zone of the reaction cell with insulated heating tape 22 (Thermolyne, Sigma) fitted with a thermocouple 24 that was connected to a temperature controller 26 (TC4S-14R). The bottom zone 14 is further covered with wool insulation 28 and wrapped with aluminum foil 30 to minimize any heat loss and temperature fluctuation. The pH of the reaction is maintained at 4.8, the optimum pH value of cellulase, using acetate buffer solution, which is checked before and after experiments to observe whether any changes in pH occurred. The pH values were 4.8 and 4.81 at the beginning and end of the experiments, respectively. Therefore, enzyme stability is assumed to be consistent throughout the process. Distilled water from a reservoir 34 at the reaction temperature is continuously passed through the system using a peristaltic pump 32, which creates the water flux cross the membrane 12. The water enters from the lowermost part of the bottom zone 14 and exits from the top of the upper zone 16 and is then collected. The water flow through the system is maintained within a low range that is found not to cause physical damage to the membrane. The weight of the water in the upper zone 16 provides an additional support against the water flux entering from the bottom cell 14. Glucose resulting from the hydrolysis may be collected from a beaker or other product collection vessel 36, as well as from the upper distilled water chamber 16.

Filter paper is used as an optimal substrate, as it contains pure alpha-cellulose and a minimal ash content of approximately 0.007%. Enzymatic cellulose hydrolysis with glucose separation, in the developed MBR 10, is compared with the reaction system without product separation. The effects of the main operational parameters, i.e., substrate concentration and water flux, on the process output variable, the glucose production yield, are determined. A total of nine experimental runs were suggested by the general factorial design. The ranges and levels of the input variables for enzymatic cellulose hydrolysis used in the Minitab software are presented in Table 1. All experiments were conducted in triplicate, and the results presented in all figures are the average values with the standard deviations shown as error bars.

TABLE 1

Two factors affecting glucose production in enzymatic hydrolysis of cellulose

| Factor level | −1 | 0 | 1 |
|---|---|---|---|
| Substrate concentration $X_1$ mg/mL | 2.67 | 6.67 | 13.33 |
| Water flux $X_2$ mL/min | 0.2 | 0.4 | 0.8 |

The determination of enzyme activity is based on glucose productivity, with one unit of cellulase being defined as the amount of glucose liberated at 37° C. and a pH of 5 in 1 h. The concentration of the liberated glucose was measured as described below and used to determine the activity of the enzyme. The activity of cellulase was determined as 1800 units/g.

The glucose concentration was measured using the DNS method, which measures the total amount of reducing sugars in a sample. In brief, 45 μL of sample is mixed with 40 μL of DNS reagent and diluted with 315 μL of distilled water to reach a total volume of 400 μL, and left to incubate for a maximum of five min at 100° C. Following stopping of the reaction with incubation in ice for ten minutes, the resulting color transformation from yellow to brown was then measured at 540 nm with a UV spectrophotometer. To further confirm the DNS measurement, the readings are compared with another method using glucose oxidase. As glucose oxidase enzymes bind specifically to glucose molecules to form gluconic acid that can be measured at 540 nm with a UV spectrophotometer, the method reads glucose concentration only. To confirm glucose quantification, two different initial substrate concentrations (6.67 and 13.3 g/L) reacting with 0.48 g/L cellulase at 48° C. and pH of 4.8 for 8 h were measured. Glucose was quantified using DNS and glucose oxidase methods, and the difference between the two readings was less than 2%.

For protein measurements, the Bradford reagent was used, an acidic Coomassie blue dye that binds stably to proteins. A spectrophotometer was used for quantification of the protein at 595 nm, which was calibrated with serial dilutions of cellulase enzymes.

The PES membrane was investigated before and after subjection to the process conditions to detect any changes that might happen. Both PES-10 and PES-30 membranes were tested before, i.e., as received, and after their use in more than 20 runs (i.e., about 160 h of operation) at different substrate concentrations and water fluxes. To detect internal fouling or any changes in the internal structure of the membrane, images of cross-sectional cuts of PES-30 are observed using a scanning electron microscope (SEM) (JCM-5000 NeoScope). Internal fouling may occur when molecules of sizes close to those of the membrane pores are pushed through, as the water is forced across the membrane, resulting in pore blockage. Neither glucose nor the substrate contribute to internal fouling, as the former is much smaller, and the latter is much larger than the membranes MWCO. If internal fouling occurs, it is mainly due to the cellulase molecules, which have molecular weights higher than the membrane cutoffs, but still in the same order of magnitude. Therefore, internal fouling is expected to be more significant as the MWCO increases and becomes closer to the size of the cellulase. As a result, the membrane with the higher MWCO, PES-30, is used and if no changes occur in the PES-30, then the same can be fairly assumed in PES-10. Samples of PES-30 before and after use are coated with gold using a JFC-1600 Auto Fine Coater (JEOL) to increase the conductivity of the nonconductive catalyst and to prevent the build-up of electrostatic charge at the specimen surface. Then, the samples are cleaned to remove silt, dust, and detritus. The samples were mounted on a holder and inserted into the scanning electron microscope for observation.

To assess surface fouling, Fourier-transform infrared (FTIR) spectroscopy (IRTracer-100 FTIR spectrophotometer) was carried out on the membrane surface. As the probability of the occurrence of this type of fouling is similar to membranes of both MWCOs, both PES-10 and PES-30 were subjected to this analysis. The FTIR spectra were recorded on an attenuated total reflection Fourier transform infrared (ATR-FTIR) spectrograph using a range of 600-4000 cm$^{-1}$ with an average of 34 scans and a spectral resolution of 4 cm$^{-1}$. X-ray diffraction (XRD) analysis was also used to measure changes in the crystalline structure of the membranes. Similar to FTIR, this test is done on both membranes, PES-10 and PES-30. XRD scans were performed with a 2θ range of 4-90°, step size of 0.02°/s, voltage of 40 kV, intensity of 20 A, and Cu Kα radiation of 1.5406 Å.

The dynamic model of the system included the following seven steps: (1) enzyme diffusion from the bulk of the bottom zone to the substrate surface; (2) enzyme binding to the substrate, both productive and nonproductive; (3) the reaction from productive binding produces the product; (4) desorption of the product from the enzyme surface to the bulk, which represents the product-inhibition effect; (5) diffusion of the product from the bulk to the membrane surface; (6) diffusion of the product through the membrane; and (7) diffusion of the product from the other side of the membrane to the bulk in the upper zone. Due to the mixing in the lower and upper zones, any convection-diffusion event (steps 1, 5, and 7) was assumed to be instantaneous. Additionally, competitive inhibition of cellulase was assumed to have been conducted by only glucose. Inhibition by the non-hydrolyzable part of the substrate, as addressed in our previous work, was not considered in this study because the substrate used was fully composed of cellulose. Cellulases, a mixture of three distinct enzymes, endoglucanase, exoglucanase, and β-glucosidase, working in synergy, were treated as a single enzyme that accomplishes complete cellulose hydrolysis. The cellulase used was *T. reesei*, which is a well-known and active cocktail identified for its high yield and production rate, and therefore is favorably used in many industrial applications.

Conventionally, extracellular cellulases from native *T. reesei* are described with low β-glucosidase activity. However, this is because β-glucosidase gets trapped in the walls of the organisms once produced and does not secrete into the culture medium where other types of cellulases are extracted and purified. Owing to the development of several techniques that showed enhanced extraction of β-glucosidase, cellulases from *T. reesei* have recently been reported to have β-glucosidase activity. The enzyme cocktail used contained β-glucosidase and has a good level of β-glucosidase activity. Therefore, the cocktail is capable of hydrolyzing β-D-glucans as well as (1,4)-β-D-glucosidic linkages. Nevertheless, a cellulase cocktail with a higher β-glucosidase activity can be used to achieve better glucose yields, which results in a better performance. Thus, the dissociation of cellobiose is assumed to be instantaneous, and its concentration and its inhibitory effect are considered negligible. This assumption was further confirmed, as previously mentioned, by comparing the DNS measurement with that found using glucose oxidase methods, which is specific to glucose detection. As mentioned, reversible binding was considered for both the adsorption and desorption steps to better represent the inhibition effect. Enzyme (E) binding to the substrate (S) is described by Eq. (1), whereas product (P) formation and desorption are described by Eqs. (2) and (3), respectively.

$$E + S \underset{k_{-s}}{\overset{k_s}{\rightleftarrows}} ES \qquad (1)$$

$$ES \overset{k_p}{\rightarrow} EP \qquad (2)$$

$$EP \underset{k_{EP2}}{\overset{k_{EP}}{\rightleftarrows}} E + P \qquad (3)$$

where $k_s$ (m$^3$g$^{-1}$h$^{-1}$) and $k_{-s}$ (1/h) are the forward and backward rate constants for reversible ES intermediate formation, respectively; $k_P$ (1/h) is the rate constant for the surface reaction step; and $k_{EP}$ (1/h) and $k_{EP2}$ (m$^3$g$^{-1}$h$^{-1}$) are the forward and backward rate constants for the competitive inhibition effect of the product on the enzyme, respectively.

Consequently, a set of first-order differential equations, Eqs. (4)-(6), could be established to describe the rate at each step of the hydrolysis, as follows:

$$\frac{d[ES]}{dt} = k_s[E][S] - (k_{-s} - k_P)[ES] \qquad (4)$$

$$\frac{d[EP]}{dt} = k_P[ES] + k_{EP2}[E][P] - k_{EP}[EP] \qquad (5)$$

$$\frac{dP}{dt} = k_{EP}[EP] - k_{EP2}[E][P] \qquad (6)$$

Eqs. (4)-(6) are similar to the ones used in our previous study, except that in the presently proposed mechanistic steps, instead of assuming EP complex formation was only due to the inhibition effect, it is assumed to be formed after the cleavage of cellulose and then dissociated to E and P. Only then does the inhibition effect occur as a result of reverse binding. This modification better represents the actual inhibition effect.

Assuming a quasi-steady-state model, the differential equations Eqs. (4)-(6) were solved simultaneously in combination with enzyme conservation given by Eq. (7), with the initial conditions of t=0, [S]=[S$_o$], and [ES]=[EP]=[P]=0. The rate of product formation was then expressed by Eqs. (8)-(13), as follows:

$$1 = E - ES - EP \tag{7}$$

$$\frac{dP}{dt} = \left(\frac{S + K_1 P}{K_2 + K_3 S + K_4 P} - k_{EP2} P\right) - P\frac{v}{V} \tag{8}$$

$$S = 1 - P \tag{9}$$

$$K_1 = \frac{(k_{-s} + k_P)k_{EP2}}{k_P k_s} \tag{10}$$

$$K_2 = \frac{\frac{k_{-s}}{k_P} - 1}{k_s} \tag{11}$$

$$K_3 = \frac{1}{k_P} + \frac{1}{k_{EP}} \tag{12}$$

$$K_4 = \frac{(k_{-s} + k_P)k_{EP2}}{k_{EP} k_s k_P} \tag{13}$$

where E, ES, and EP are the dimensionless mass concentrations of the total cellulase, enzyme substrate complex, and enzyme product complex, respectively, defined as the respective concentrations in the reaction cell, [E], [ES], and [EP], divided by the initial enzyme concentration, [Eo]; P and S are the dimensionless concentrations of the product and substrate, defined as the concentrations of the glucose, [P], and the substrate, [S]), in the reaction cell divided by the initial substrate concentration, [So]), respectively; V is the volume of the reaction cell; v is the superficial velocity of flowing water in the system; and t is the time.

The total glucose yield (Y) can be then described using Eq. (14), which is the sum of the mass of glucose accumulated in the reaction cell and of that diffused to the upper cell divided by the initial mass of the substrate.

$$Y = \frac{G}{[S_0]V} = P + \frac{v}{V}\int_0^t P \, dt \tag{14}$$

Figure 3A:
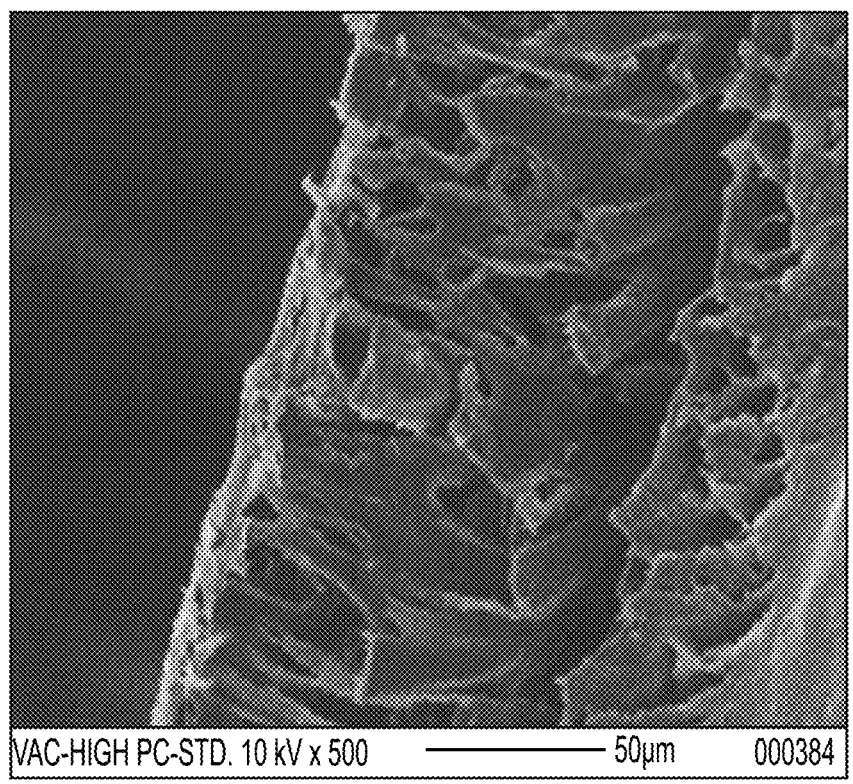
FIGS. 3A and 3B are scanning electron microscopy (SEM) photomicrographs through a section of a polyethersulfone (PES) membrane before and after enzymatic hydrolysis of cellulose in the membrane bioreactor of FIG. 1, respectively.
Figure 3B:
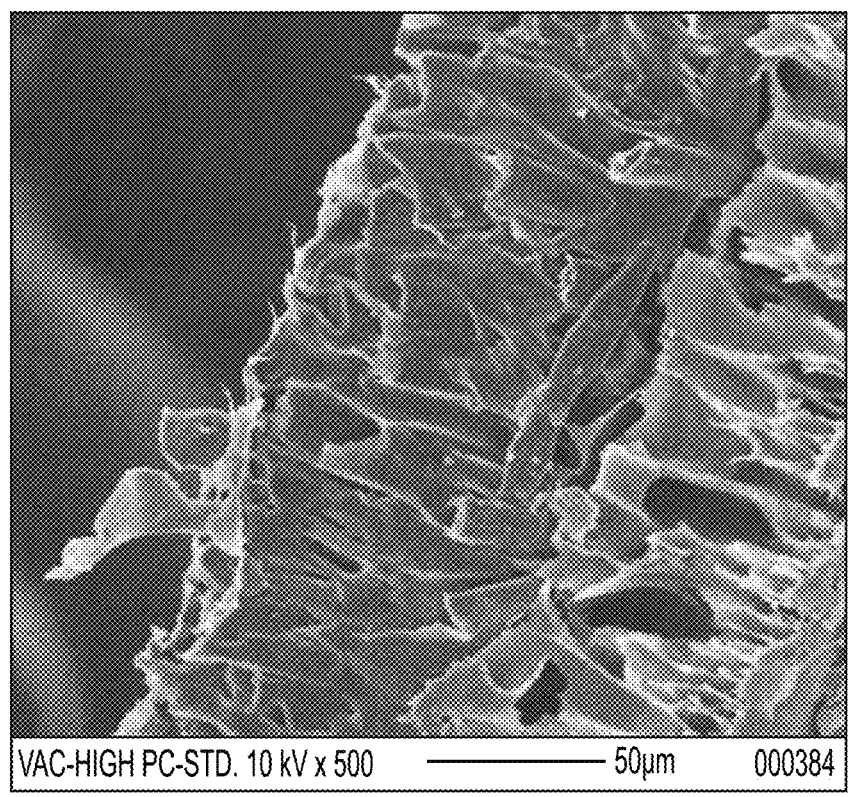
Figure 4A:
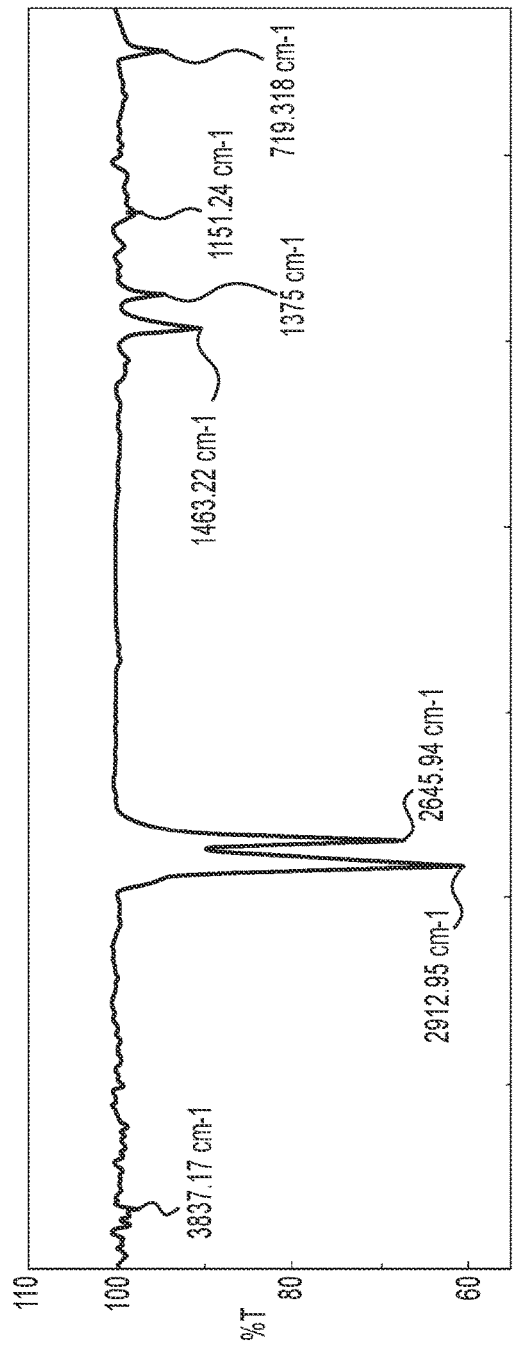
FIGS. 4A and 4B are FTIR spectra of a PES-10 membrane before (FIG. 4A) and after (FIG. 4B) use of the membranes in the membrane bioreactor of FIG. 1 for enzymatic hydrolysis of cellulose.
Figure 4B:
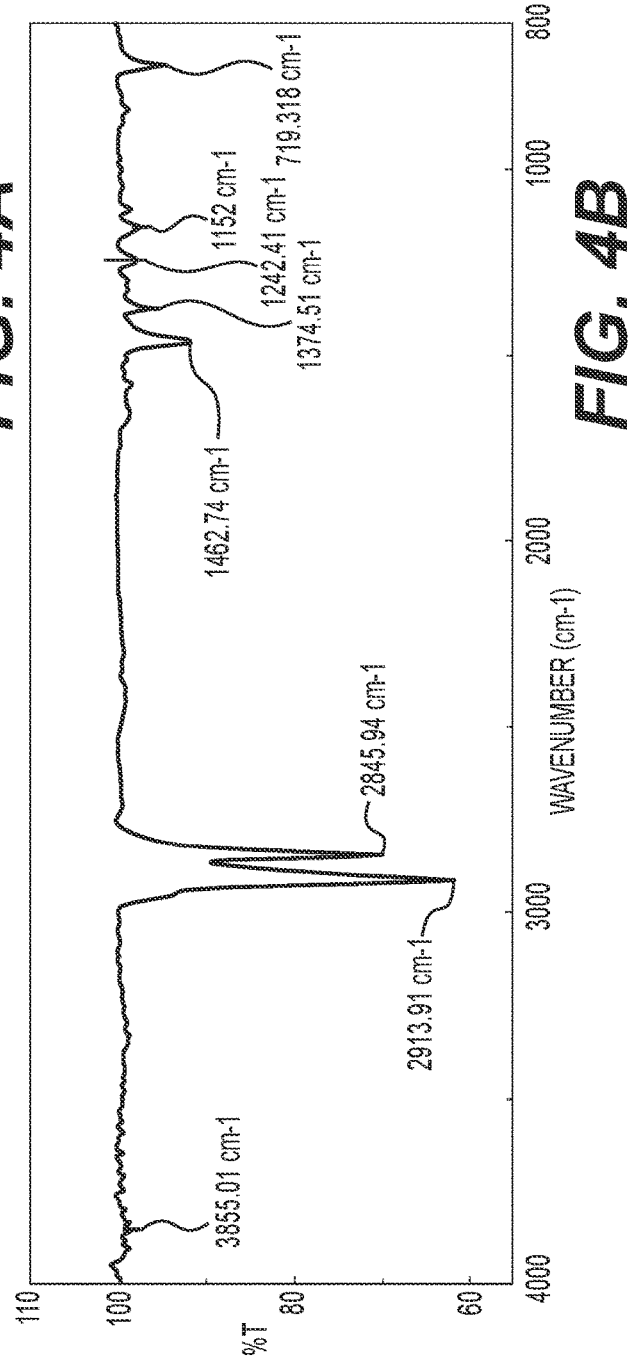

The designed MBR with the PES membrane was subjected to glucose permeation and cellulase rejection analyses. Theoretically, PES membranes should selectively allow permeation of the relatively small glucose molecules (180 Da) and reject the larger molecules of cellulase comprising endoglucanase (~52,000 Da), exoglucanase (61,000 Da), and β-glucosidase (76,000 Da). Indeed, the PES membrane with 10 kDa MWCO (PES-10) has previously shown to allow the complete permeation of glucose and the total rejection of cellulase. To further confirm this, the permeation of glucose and cellulase through a PES membrane with larger MWCO membrane of 30 kDa MWCO (PES-30) was investigated. FIGS. 3A and 3B show the permeated yields of glucose and cellulase in the upper portion of the MBR cell over time the using the PES-30 membrane with initial glucose and cellulase concentrations of 40 g/L and 3.2 g/L, respectively, and water flux of 0.4 mL/min. The lines shown on the figure are connection between the points, added to highlight the trend. Within 16 h, approximately 50% of the added glucose had permeated to the upper chamber, whereas no cellulase was detected therein.

To eliminate the possibility of cellulase being pushed into the pores of the membrane, resulting in internal fouling and a drop in the enzyme bulk concentration, the cellulase concentration in the reaction cell was measured while using the PES-10 membrane. This experiment was conducted using initial glucose and cellulase concentrations of 67 g/L and 0.48 g/L, respectively, and the highest water flux used in this work of 0.8 mL/min. As the diffusion of molecules into the membrane pores occurs more easily when the pore size is close to the size of the enzyme molecule, the experiment was repeated using a membrane with a 50 kDa MWCO (PES-50). With both membranes, there was no drop in cellulase concentration detected (data not shown), which confirmed that the diffusion effect was negligible, and the PES membrane had completely rejected cellulase permeation. Another important conclusion that can be made here was the insignificance of the membrane MWCO effect on the process within the investigated MWCO range, especially in the case where the convection/diffusion of glucose was greater than its molecular diffusion, which was also confirmed in this work as explained below.

To confirm that the internal fouling effect was not significant and that subjecting the membrane to the reaction system did not affect the morphology of the membrane, damage it or the internal structure has been changed, SEM images of the PES-30 membrane were acquired before, i.e., as commercially received (FIG. 3A), and after (FIG. 3B) its use in multiple experiments with different substrate concentrations and water fluxes. The cross-sectional SEM images showed no significant changes in the morphology of the PES-30 membrane after subjection to the reaction systems (FIGS. 3A, 3B). Therefore, it can be assumed that internal fouling effect was insignificant, which is expected with the low range of water flow rate used.

The absence of surface fouling was also confirmed by analyzing the chemical changes that may have occurred on the membrane during the processes of enzymatic hydrolysis and diffusion using FTIR, as well as to detect enzyme immobilization, as FTIR is a common technique used to detect enzyme immobilization on membranes. FIGS. 4A-4D show the FTIR spectra (range: 600-4000 cm$^{-1}$) of the PES-10 and PES-30 membranes before and after the enzymatic hydrolysis. The spectra of both the PES membranes agreed with those reported in other studies, in which the sustainment of the peaks similar to that found in this work for the membranes before and after subjection to reaction conditions were taken as evidence for absence of surface fouling. The peaks at 2913 and 2845 cm$^{-1}$ represent the phenoxy groups that form the backbone of the PES membrane. The peak at 1374 cm$^{-1}$ is a characteristic of —CH3 bending; the peak at 1152 cm$^{-1}$ can be assigned to the asymmetrical stretching vibration of sulfonic acid groups found in the PES membrane; and the peak at 719 cm$^{-1}$ belongs to aromatic carbons.

The spectra of the membranes before and after the reaction generally showed similar peaks. The only changes observed after the process were the appearance of a peak at 1242 cm$^{-1}$ in PES-10 due to the asymmetrical stretching of aromatic Ar—O—Ar ethers and the disappearance of the peak at 1651 cm$^{-1}$ in PES-30 due to the vibration of the amide group. The latter has been reported to be a characteristic of polyvinylpyrrolidone, a material added to the PES membrane. However, these changes were minor and do not suggest any significant change in the PES membrane characteristics following its use in the reaction process. The absence of internal fouling was further confirmed by measuring the protein concentration in the lower cell at the beginning and at the end of the reaction. As no drop in the concentration was detected, it was fairly assumed that enzyme adsorption on the membrane is negligible. This further confirmed the results of the FTIR, which also suggested no presence of adsorbed enzyme.

Figure 5:
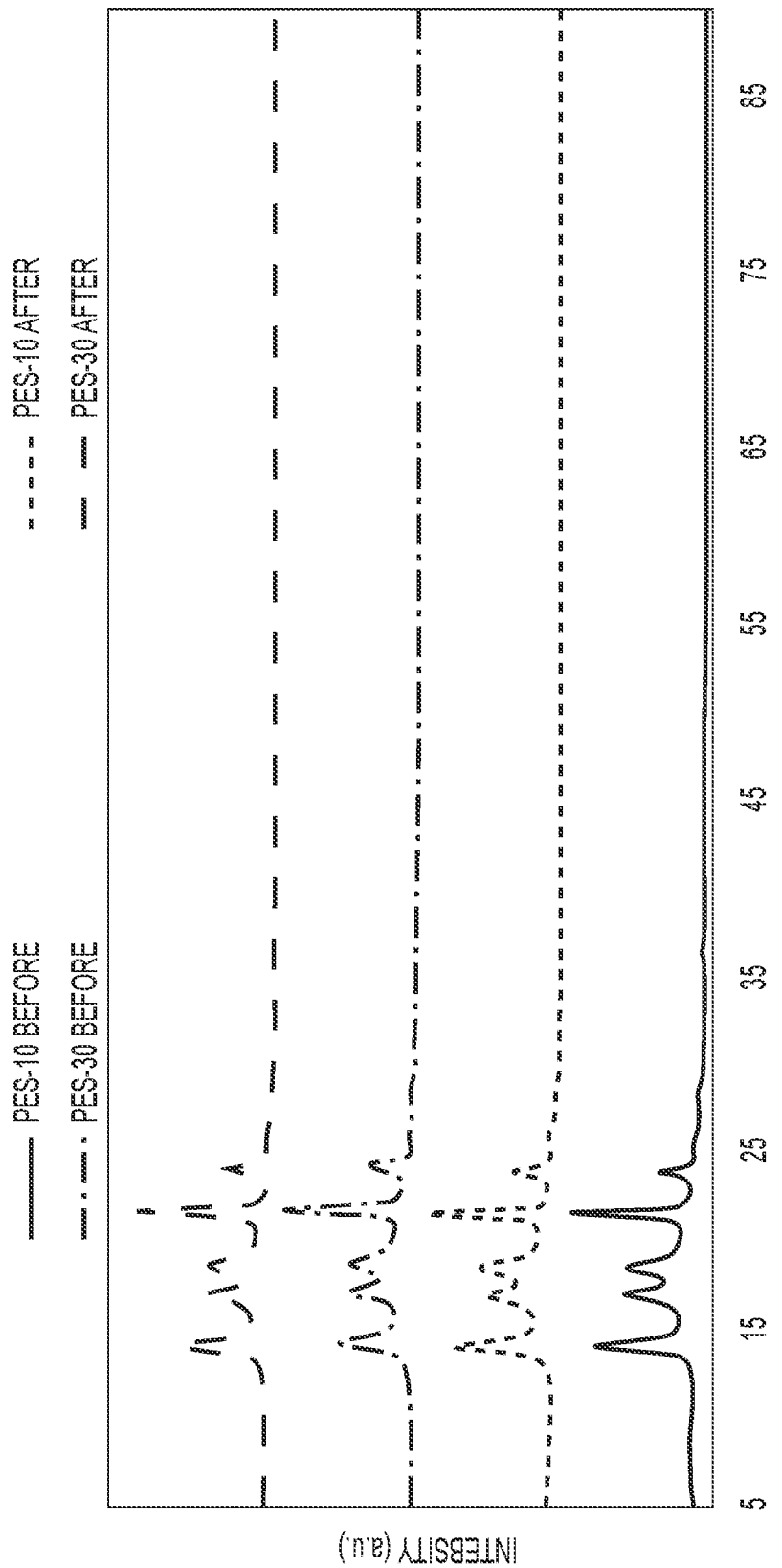
FIG. 5 is a composite X-ray diffractogram of PES-10 and PES-30 membranes before and after enzymatic hydrolysis of cellulose in the membrane bioreactor of FIG. 1.

The aforementioned findings were further confirmed using XRD analysis, which was carried out to investigate changes in the crystalline structure of the membrane. As shown in FIG. 5, there were no clear changes in the XRD spectra for either PES-10 or PES-30 membranes before and after enzymatic substrate hydrolysis, proving that they were not affected by the reaction process.

Figure 6:
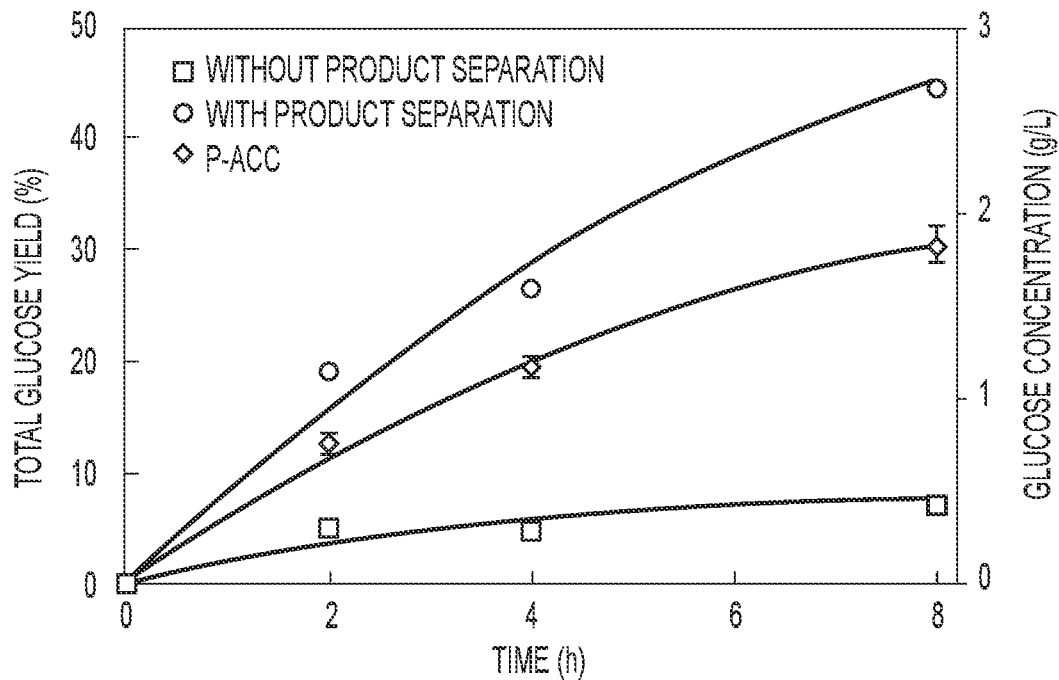
FIG. 6 is a composite plot of glucose production yields and glucose concentration (g/L) after enzymatic hydrolysis of cellulose in the membrane bioreactor of FIG. 1. with or without glucose separation.

To prove the concept of enhanced enzymatic hydrolysis with simultaneous product separation, the experiment was run at 48° C. using the PES-10 membrane, 6.67 g/L of filter paper as pieces, 0.48 g/L of *T. reesei* cellulase, and a water flux of 0.4 mL/min. The results were compared with a reaction conducted under the same conditions but without product separation. As shown in FIG. 6, a total glucose yield of 45% was achieved within 8 h in the MBR with product separation, whereas the yield did not exceed 7% in the reactor without product separation. The lines shown on the figure are connections between the points, added to highlight the trend. It should be noted that the error bars were too small to be observable at the various data points of the curve, which indicates good reproducibility of the data. The results clearly prove the concept and highlight the crucial effect of product or glucose inhibition on the enzymatic activity.

Figure 7:
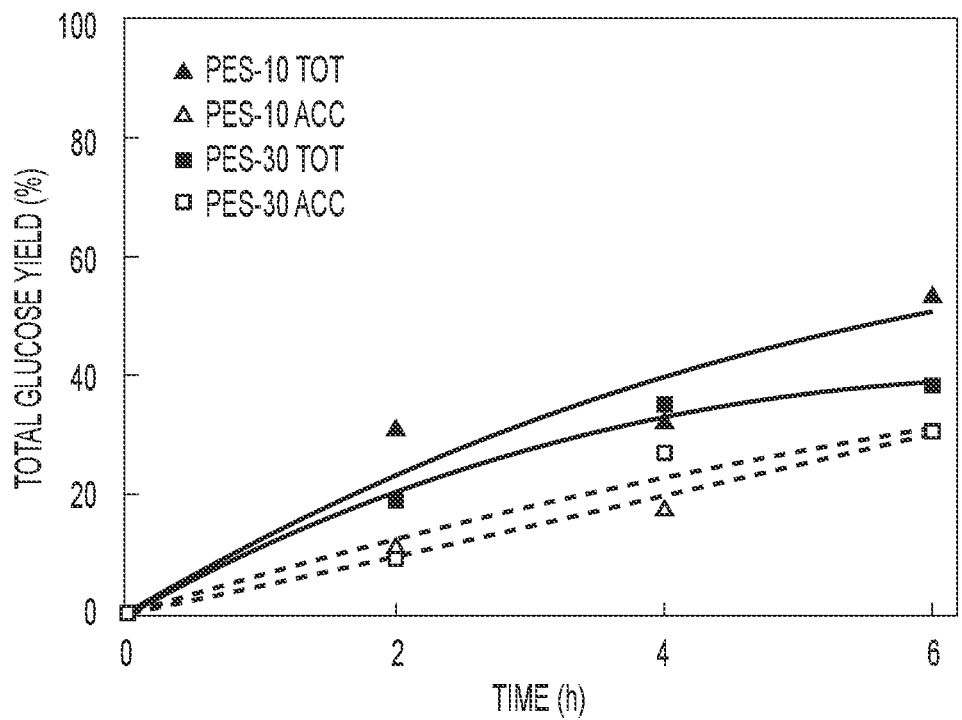
FIG. 7 is a composite plot of total glucose yields and accumulated glucose produced in the reaction cell of the membrane bioreactor of FIG. 1 after enzymatic hydrolysis of cellulose using PES-10 and PES-30 membranes.

To confirm that the dominant factor for product separation was convection flow and that the effect of MWCO and internal fouling were negligible, the simultaneous hydrolysis-product separation experiment was repeated using membranes of different MWCO, under the same reaction conditions of 48° C., water flux of 0.4 mL/min, and initial substrate and cellulase concentrations of 6.67 g/L and 0.48 g/L, respectively. Internal fouling is expected to be more significant as the MWCO increases and become closer to the size of the cellulase. Therefore, should this effect be significant, the behavior of membranes of different MWCOs would have been different, with PES-30 displaying a lower permeability. However, as shown in FIG. 7, similar results were obtained using both membranes, which supports our assumption that the convection flow was the dominant permeation mechanism, the effect of MWCOs was confirmed to be insignificant, and further supports our previous finding that internal fouling was not significant.

Figure 8A:
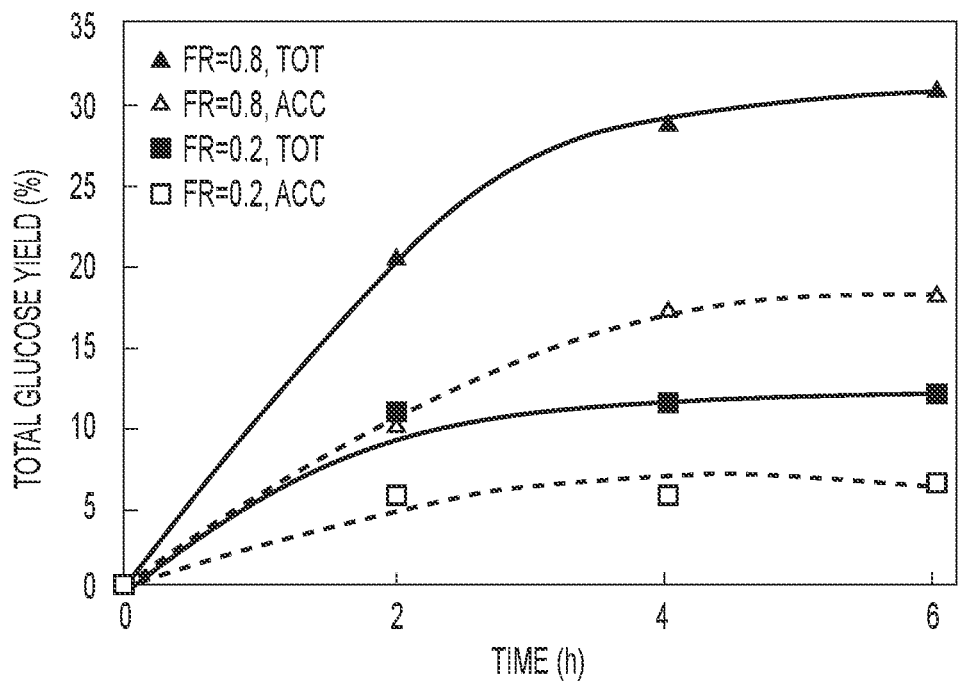
FIGS. 8A is a composite plot of total glucose yields and accumulated glucose produced in the reaction cell of the membrane bioreactor of FIG. 1 after enzymatic hydrolysis of cellulose using a PES-10 membrane, constant substrate and enzyme concentrations, and different water fluxes.

The effects of different water fluxes and substrate concentrations on product concentration as a function of time and on product yield after 6 h were measured using the PES-10 membrane at the levels listed in Table 1. A few runs were repeated using the PES-30 membrane to further confirm the insignificance of the membrane MWCO effect. FIG. 8A shows the effects of two different water fluxes on the total glucose yield and the glucose yield in the reaction cell using the PES-10 membrane at an initial substrate concentration of 13.3 g/L. The curves clearly show that total production increased with an increase in the water flux. This was mainly due to an increase in product removal, which had a positive effect in reducing enzyme inhibition by the product and pushing the reaction forward.

Figure 8B:
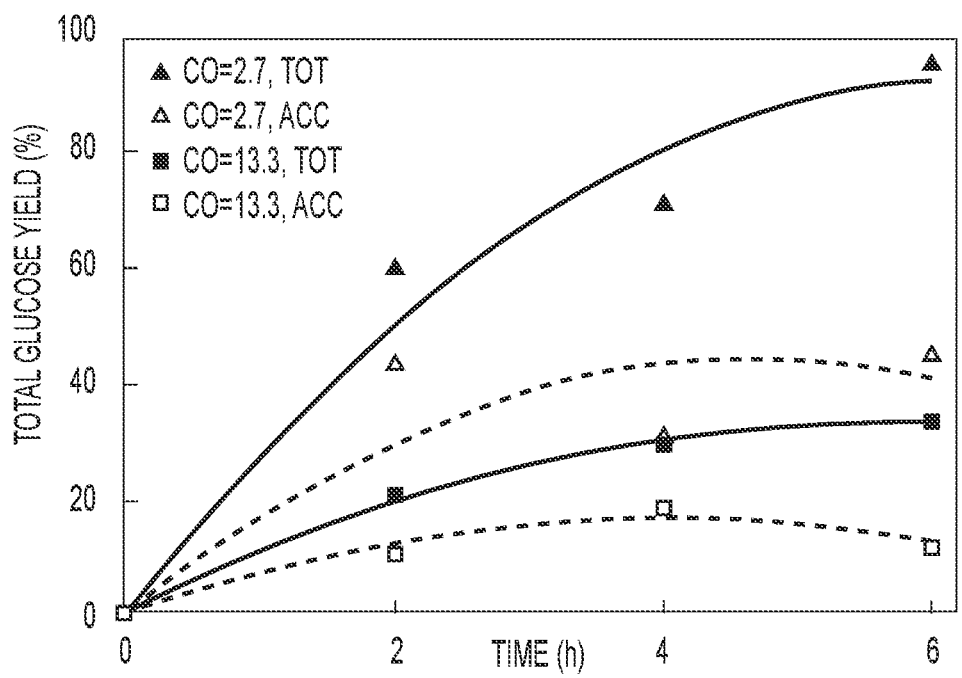
FIG. 8B is a composite plot of total glucose yields and accumulated glucose produced in the reaction cell of the membrane bioreactor of FIG. 1 after enzymatic hydrolysis of cellulose using a PES-10 membrane, the same water flux, and different substrate concentrations.

FIG. 8B shows the effects of two different initial substrate concentrations (2.7 and 13.3 g/L) on the total glucose yield and the glucose yield in the bottom portion of the MBR cell using PES-10 at a water flux of 0.8 mL/min. The results showed that increasing the substrate concentration positively affected glucose production in the reaction cell. This is the general behavior of chemical reactions, where an increase in the reacting molecules to form the products will push the reaction forward. The slight drop in the curve observed toward the end of the observation period for the 2.7 g/L substrate concentration was due to the dilution effect. At the beginning of the reaction, the product was produced at a rate faster that the dilution effect generated by the introduced water flux, allowing the accumulation of the product, and hence an increase in its concentration. After some time, the rate of product formation decreased, and the dilution effect became more prominent, resulting in the observed drop in the product concentration in the reaction chamber. This was obviously not the case with the total glucose yields, which continued to increase, as shown in FIG. 8B.

However, the effect of increasing the substrate concentration had an opposite effect on the total glucose yield. This should not be mistakenly attributed to the substrate concentration. It is because the yield did not increase linearly with the increase in substrate concentration. Hence, a division of the yield data by the initial amount of substrate used resulted in the observed yield decrease. In the present study, the maximum substrate concentration used in the MBR was 13.3 g/L. A higher concentration required a more vigorous agitation, which was avoided to eliminate high stresses on the enzyme that could cause denaturation. For industrial applications, however, a higher substrate loading with an enhanced yield may be needed. To achieve this, semi-batch additions of substrate could be used to maintain the concentration of substrate at its optimum value, coupled with using a cellulase cocktail with a higher β-glucosidase activity.

Figure 9A:
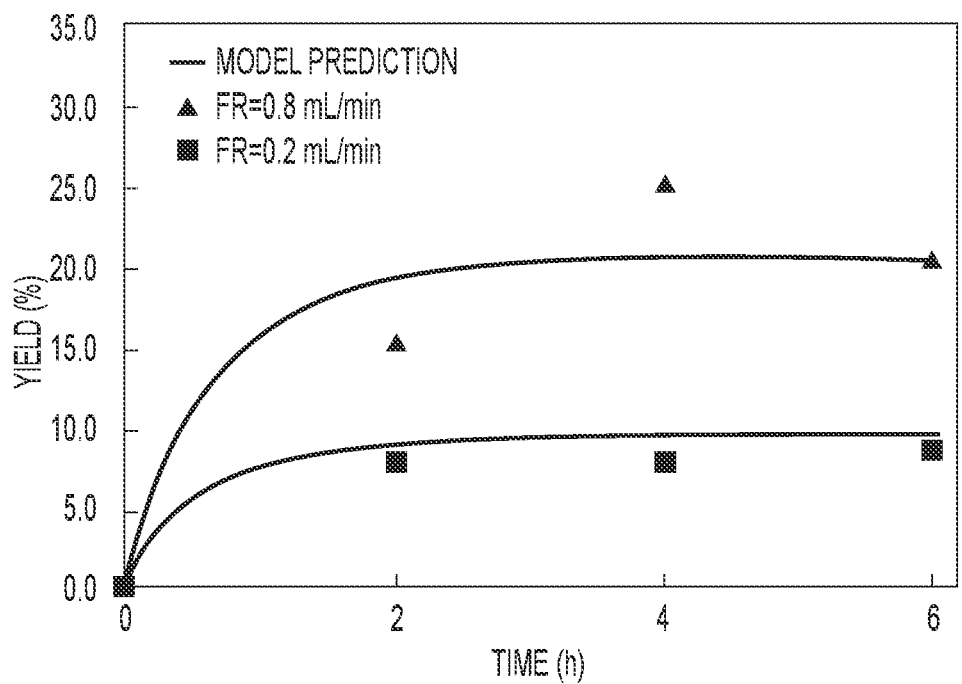
FIG. 9A is a composite plot comparing a kinetic model prediction of total glucose yield with experimental data for enzymatic hydrolysis using the membrane bioreactor of FIG. 1 with initial water fluxes of 0.2 mL/min and 0.8 mL/min, respectively, as a function of time.
Figure 9B:
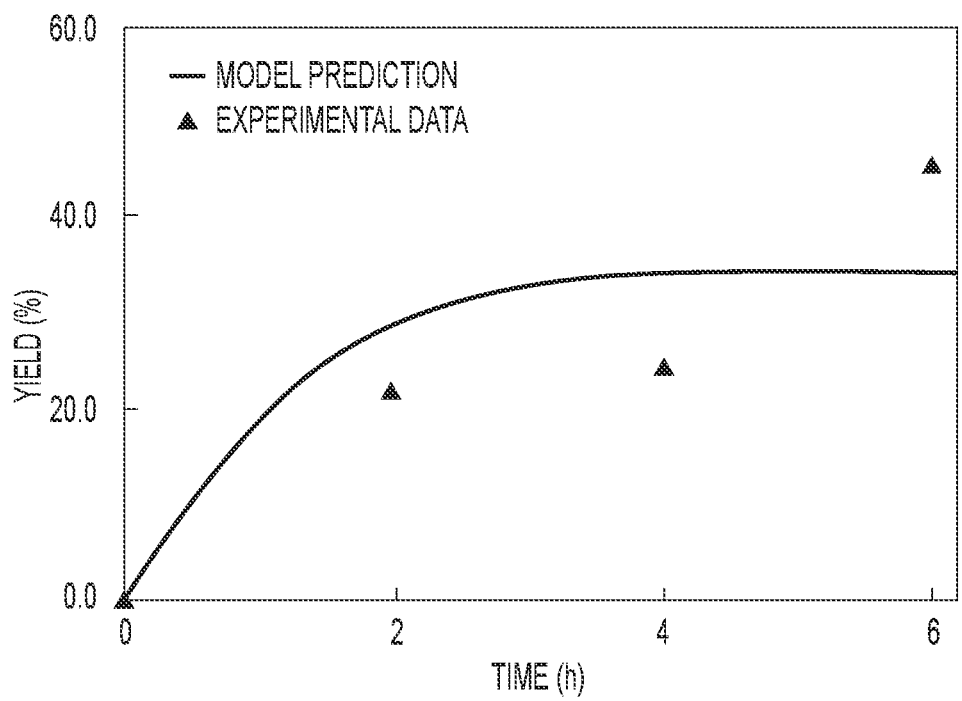
FIG. 9B is a composite plot comparing a kinetic model prediction of total glucose yield with experimental data for enzymatic hydrolysis using the membrane bioreactor of FIG. 1 with initial substrate concentration of 6.67 g/L and initial water flux of 0.4 mL/min, respectively, as a function of time.

The Polymath software was used to determine the numerical values of the parameters in Eq. (8). The equation was solved using estimated kinetic parameters, which were changed to minimize the error between the experimental results and the model predictions. The determined parameters are presented in Table 2, and comparisons between the experimental data and the model predictions are presented in FIGS. 9A, 9B. The figures show the total glucose yields at different initial substrate concentrations and water fluxes as (A) 13.3 g/L and 0.2 mL/min, (B) 13.3 g/L and 0.8 mL/min, and (C) 6.67 g/L and 0.4 mL/min, respectively, using the PES-10 membrane with the 0.48 g/L cellulase at 48° C. and a pH of 5. The results showed that the developed kinetic model with the determined parameters could largely predict the experimental data. As shown in Table 3, a comparison of the yields after 6 h resulted in an $R^2$ value of 0.96, which was close to that found using the statistical model. As a result, a kinetic model developed from mechanistic reaction steps that can be used to describe the behavior of the complex enzymatic hydrolysis of cellulose in a MBR with simultaneous product separation.

TABLE 2

Estimates of kinetic model parameters

| Kinetic parameter | Value | Unit |
|---|---|---|
| $k_s$ | $3.5 \times 10^{-2}$ | $m^3 g^{-1} h^{-1}$ |
| $k_{-s}$ | 0.33 | 1/h |

TABLE 2-continued

Estimates of kinetic model parameters

| Kinetic parameter | Value | Unit |
|---|---|---|
| $K_P$ | 0.33 | 1/h |
| $K_{EP}$ | 0.5 | 1/h |
| $K_{EP2}$ | $9.0 \times 10^{-3}$ | $m^3 g^{-1} h^{-1}$ |

TABLE 3

Total glucose yield after 6 h at different substrate concentrations and water fluxes

| Substrate concentration (g/L) $X_1$ | Water flux (mL/min) $X_2$ | Observed yield (%) | Statistical yield (%) | $R^2$ | Model yield (%) | $R^2$ |
|---|---|---|---|---|---|---|
| 2.67 | 0.2 | 64.45 ± 0.03 | 64.46 | 0.97 | — | 0.96 |
| 13.33 | 0.2 | 8.33 ± 0.008 | 8.39 | | 15.08 | |
| 2.67 | 0.8 | 86.63 ± 0.017 | 86.65 | | — | |
| 13.33 | 0.8 | 20.40 ± 0.016 | 20.47 | | 17.98 | |
| 6.67 | 0.4 | 44.75 ± 0.038 | 32.61 | | 37.49 | |

Response surface regression analysis was performed using the Minitab 19 software with the statistical significance established at a P-value of <0.05. Table 4 shows the results of the analysis of variance obtained after examining the effects of two independent variables, i.e., substrate concentration ($X_1$) and water flux ($X_2$), on the total glucose yield after 6 h of hydrolysis. The linear effects of both the substrate concentration and water flux were found to be significant. The substrate concentration effect was more significant. The quadratic term of the substrate concentration ($X_1^2$) was also significant (P=0.07), whereas the concentration of the water flux ($X_2^2$) was not estimated and removed from the model because of the sample size. This was indicative that, unlike the water flux effect, the substrate concentration effect would have a parabolic shape. It was also found that both $X_1$ and $X_{1\times 2}$ negatively contributed to the yield of the glucose production, which agreed with the previous observation of enzyme hydrolysis and product separation.

TABLE 4

Response surface regression analyses of product yield versus substrate concentration ($X_1$ and water flux ($X_2$): (A) coded coefficients; (B) analysis of variants.

| Term | Coef | SE Coef | T-Value | P-Value | VIF |
|---|---|---|---|---|---|
| Constant | 26.89 | 2.91 | 9.22 | 0.000 | |
| $X_1$ | −30.59 | 3.14 | −9.73 | 0.000 | 1.04 |
| $X_2$ | 8.56 | 3.14 | 2.72 | 0.035 | 1.07 |
| $X_1 * X_1$ | 18.07 | 4.44 | 4.07 | 0.007 | 1.11 |
| $X_1 * X_2$ | −2.53 | 3.14 | −0.80 | 0.452 | 1.00 |
| Source | DF | Adj SS | Adj MS | F-Value | P = Value |
| Model | 4 | 4451.00 | 1112.75 | 28.13 | 0.000 |
| Linear | 2 | 4035.73 | 2017.87 | 51.02 | 0.000 |
| $X_1$ | 1 | 3742.55 | 3742.55 | 94.62 | 0.000 |
| $X_2$ | 1 | 293.18 | 293.18 | 7.41 | 0.035 |
| Square | 1 | 655.42 | 655.42 | 16.57 | 0.007 |
| $X_1 * X_1$ | 1 | 655.42 | 655.42 | 16.57 | 0.007 |
| 2-way interaction | 1 | 25.57 | 25.57 | 0.65 | 0.452 |
| $X_1 * X_2$ | 1 | 25.57 | 25.57 | 0.65 | 0.452 |
| Error | 6 | 237.32 | 39.55 | | |
| Total | 10 | | | | |

Coef, coefficient;
SE Coef, standard error of the coefficient;
VIF, variance inflation factor;
DF, degrees of freedom;
Adj SS, adjusted sum of the squares;
Adj MS, adjusted mean square.

A second-order interactive regression model, Eq. (15), was developed to relate the product yield (Y) and the two independent parameters, X1 and X2. The equation was used to draw a three-dimensional (3D) plot of the combined effects of substrate concentration and water flux on the total glucose yield, as in FIGS. 8A and 8B.

$$\text{Yield}(\%) = 92.9 - 0.15.12\, X_1 + 41.2\, X_2 + 0.636\, X_1^2 - 1.58\, X_1 X_2 \quad (15)$$

Figure 10:
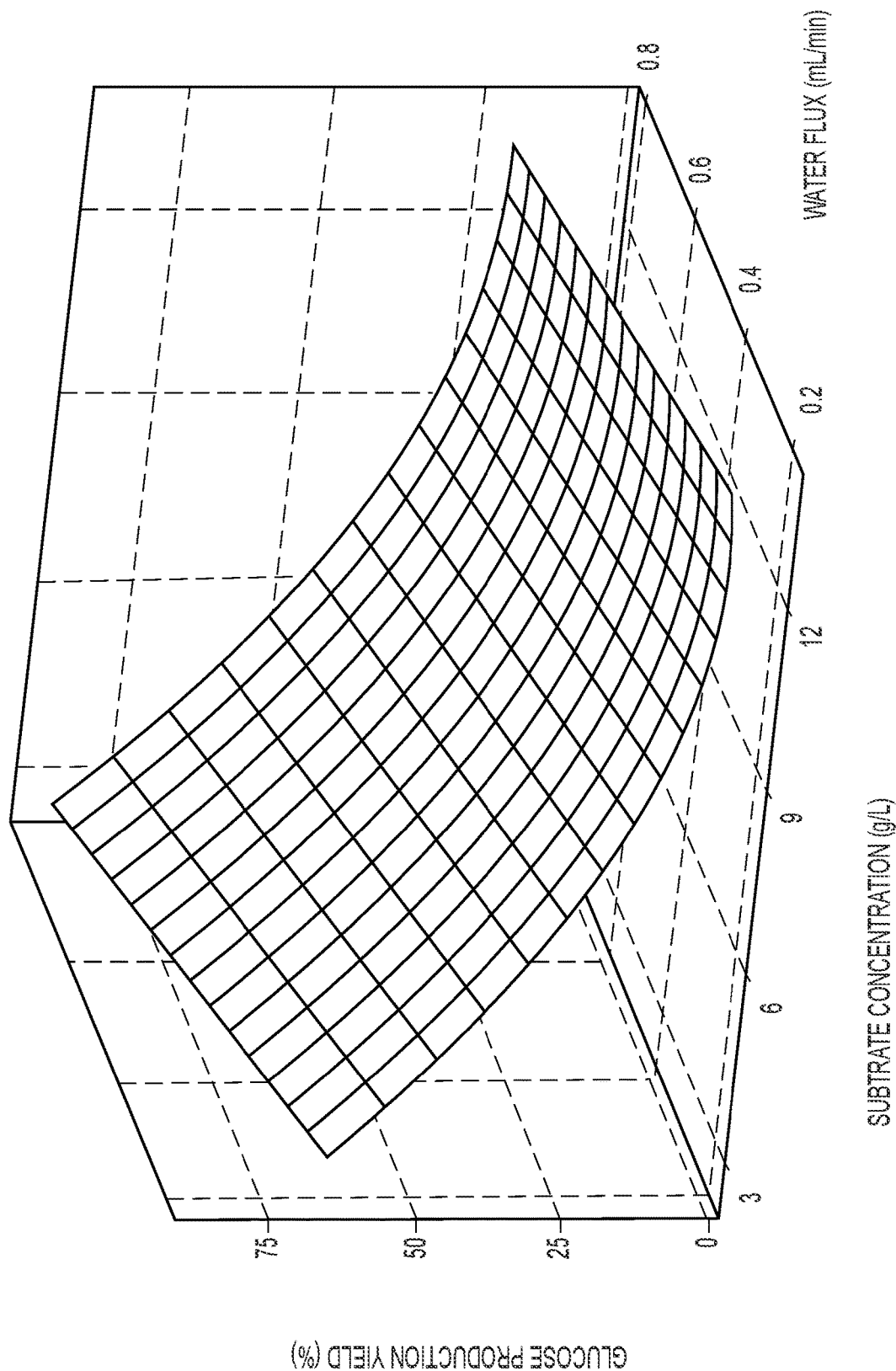
FIG. 10 is a three-dimensional plot of total glucose yields as a function of the substrate concentration and water flux after 6 h of enzymatic hydrolysis using the membrane bioreactor of FIG. 1 with a PES-10 membrane for product separation.

The process was optimized using Response Optimizer in Minitab, which showed that the lowest substrate concentration (2.67 g/L) and the highest water flux (0.8 mL/min) would result in the maximum yield of 86.65% (Table 3). The experimental results agreed closely with the model prediction and obtained an actual yield of 86.63±0.017%. These results agreed with the 3D surface graph, as shown in FIG. 10, which also showed the positive effect of the water flux and the negative effect of the substrate concentration on the yield. This figure also showed that the substrate concentration effect was more significant than the water flux effect, which agreed with the P-values discussed above.

In this disclosure, an MBR using PES membranes with different MWCOs in an inverted dead-end filtration concept was designed. The membrane system was shown to completely reject cellulase and only allow the permeation of glucose. The successful separation of glucose by the membrane enhanced enzymatic cellulose hydrolysis by T. reesei cellulase relative to the level achieved with the traditional batch reactor with no separation. The continuous removal of the product eliminated the product-inhibition effect and pushed the reaction forward. Statistical analysis of the two main factors affecting the glucose production yield, initial substrate concentration and water flux, showed the significance of both factors to the reaction system. The kinetic model developed from the mechanistic reaction steps was successfully fitted to the experimental data. The successful results provide a theoretical basis that can be used by one of ordinary skill in the art to significantly enhance the enzymatic hydrolysis of cellulose, which is vital to the high-yield production of bioethanol from lignocellulosic biomass. This disclosure can be a starting point to further develop and understand the designed MBR. A real lignocellulosic biomass can be used to address real reaction, which extends our understanding for industrial production. In this study, PES membrane was used. However, further modifications to the design would obviously include other types of membranes, such as ceramic membranes, which would provide better mechanical properties. In addition, using cellulase cocktails with a higher β-glucosidase activity, in combination with semi-batch substrate additions, could also be tested for improvement of the system's performance.

Figure 11:
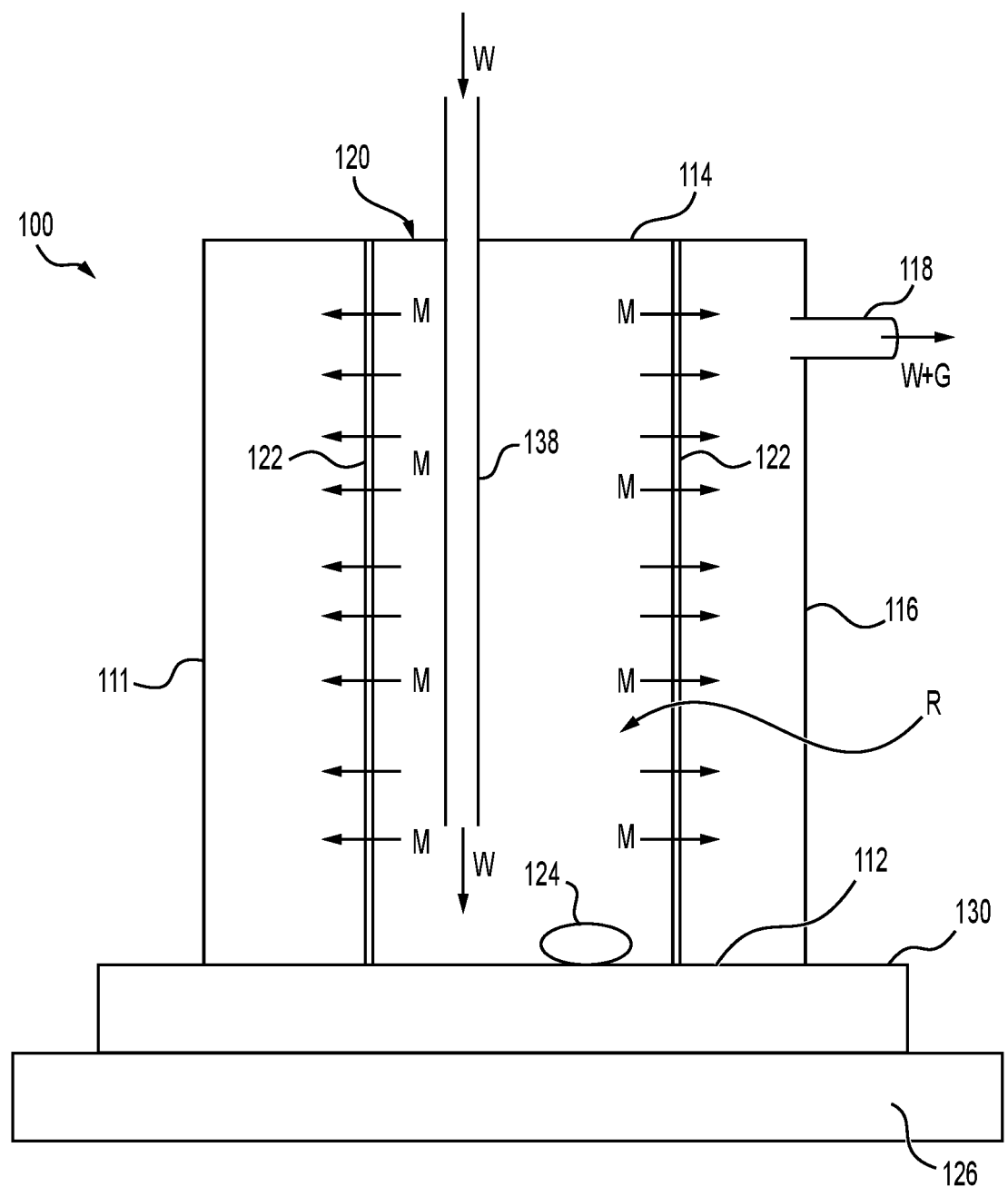
FIG. 11 is a schematic diagram of an alternative embodiment of a membrane bioreactor for simultaneous enzymatic cellulose hydrolysis and product separation configured as a radial-flow membrane bioreactor.

In an alternative embodiment, the membrane bioreactor for simultaneous enzymatic cellulose hydrolysis and product separation is configured as a radial-flow membrane bioreactor for enzymatic cellulose hydrolysis and product separation. The radial-flow membrane bioreactor for enzymatic cellulose hydrolysis and product separation 100 is a bioreactor for producing a biofuel intermediate, such as glucose, through bacterial-based enzymatic hydrolysis of a cellulose biomass. The produced glucose can then be converted into the biofuel ethanol, for example. As shown in FIG. 11, the radial-flow membrane bioreactor 100 includes a hollow housing 111 having a lower wall 112, an upper wall 114 and a cylindrical sidewall 116. The cylindrical sidewall 116 has an outlet port 118 mounted therein, and the upper wall 114 has an inlet port 120 extending into the housing 111. A cylindrical filter 122 is mounted concentrically within the cylindrical hollow housing 111 and extends between the lower wall 112 and the upper wall 114. The cylindrical filter 122 is formed from a semipermeable polyethersulfone membrane.

In use, water W may be delivered into a reaction region R defined by the cylindrical filter 122 through a conduit 138 extending through the inlet port 120, extending from outside the hollow housing 111 into the reaction region R. The cellulose biomass and the enzyme medium (cellulase) for performing enzymatic hydrolysis on the cellulose are also placed within the reaction region R. Initially, the region outside of the reaction region R (i.e., a cylindrical annulus defining a product collection region between the cylindrical filter 122 and the inner face of sidewall 116) may be filled with distilled water at a pH similar to that inside the reaction region R. This region is filled with water such that the water completely covers the surface of the cylindrical filter 122.

The biofuel intermediate, such as glucose or the like, produced by the enzymatic hydrolysis process mixes with the water, and this mixture M flows radially outward through the cylindrical filter 122, which filters any additional reaction products and/or remnants of the reactants, into an annular product collection or recovery zone surrounding the cylindrical filter 122. The mixture M flows through the entirety of the surface of the cylindrical filter 122 in the radial direction. The outlet port 118 releases the hydrolysis product containing only water W and glucose G, where the water W may then be separated out. The input of fresh water W and the output of the mixture of water W and glucose G is carefully matched to ensure that no pressure differential exists across the cylindrical filter 122.

Figure 13:
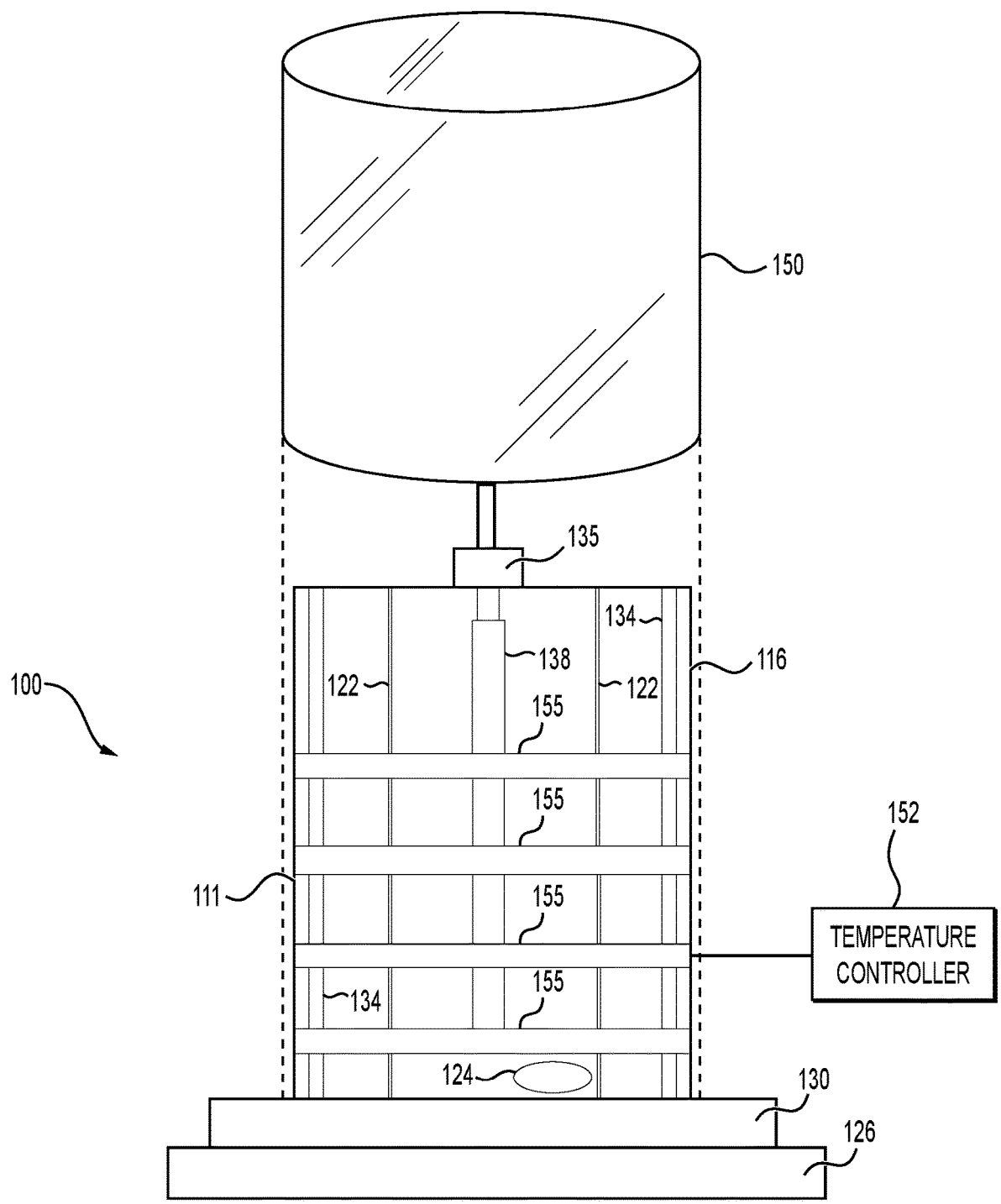
FIG. 13 is a schematic diagram of an alternative embodiment of a radial-flow membrane bioreactor.

Within the reaction region R, the mixture M may be stirred by any suitable type of stirrer or mixer. For example, a magnetic stirrer may be used. In the non-limiting example of FIG. 11, the magnetic stirrer 124 is disposed within the reaction region R inside the hollow housing 111, and the hollow housing 111 rests on a magnetic stirring plate 126. The mixture and the reactants may also be heated within the reaction region R by any suitable type of heating device. For example, the magnetic stirring plate 126 may be combined with or have a built-in heating coil to form a hot plate, as is well-known in the art. In FIG. 13, additional controlled heating is provided by heating tape 155 wrapped around the cylindrical sidewall 116 of hollow housing 111. For example, one such heating tape is sold under the name Thermolyne®, which is silicone rubber-encapsulated heating tape, manufactured by Millipore Sigma®. The heating tape 155 may be fitted with a thermocouple and be connected to an external temperature controller 152. An exemplary temperature controller is the TC4S-14R temperature controller, manufactured by Autonics®.

In the experiments, a stirring speed using magnetic impeller 124 of 450 rpm was found to create enough turbulence for good mixing, while avoiding shear stress that could deactivate the enzymes. During these experiments, the temperature of the reaction was maintained at 48° C. using the combined hot plate and magnetic stirrer 126 and heating tape 155, as described above. The water W entering the reaction region R through conduit 138 was distilled water at the reaction temperature and adjusted to a pH of 5, pressurized by an external peristaltic pump. During the experiments, the active membrane surface area of cylindrical filter 122 was 578 $cm^2$, and the specific area per volume of reaction within reactor 100 was 0.62 $cm^2/cm^3$.

As further shown in FIG. 13, an insulating jacket 150 may be removably wrapped around the hollow housing 111. It should be understood that any suitable type of insulator may be used to minimize heat loss and/or temperature fluctuations. For example, the insulating jacket 150 may be formed from wool insulation wrapped with aluminum foil.

Figure 12:
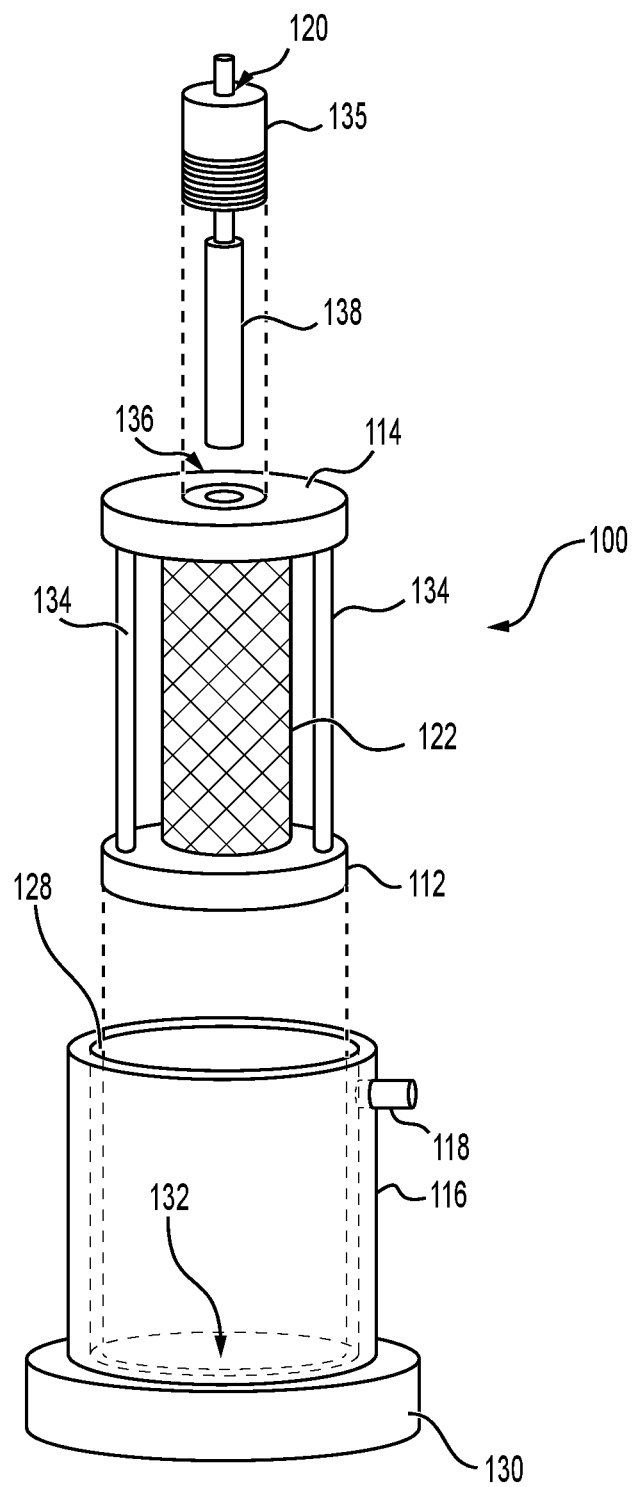
FIG. 12 is a partially exploded perspective view of the radial-flow membrane bioreactor of FIG. 11.

It should be understood that the general arrangements illustrated diagrammatically in FIGS. 11 and 13 may be assembled or constructed in any suitable manner. In FIG. 12, the upper wall 114 of the hollow housing 111 is formed as an upper disc, which is releasably sealed to an inner surface 128 of the cylindrical sidewall 116. Similarly, the lower wall 112 of the hollow housing 111 is formed as a lower disc, which is releasably sealed to the inner surface 128 of the cylindrical sidewall 116. The radial-flow membrane bioreactor 100 may be further provided with a base 130 having a recess 132 formed therein. The hollow housing 111 is mounted on the base 130 such that the lower disc 112 is releasably placed within the recess 132.

As further shown in FIG. 12, at least one support 134 (a stud or column) is attached to and extends between the upper disc 114 and the lower disc 112. In FIG. 12, a pair of supports 134 are shown, although it should be understood that any suitable number of supports 134 may be used. Additionally, a stopper 135 removably seals a passage 136 formed through the upper disc 114, the inlet port 120 extending through the stopper 135. In FIG. 12, the stopper 135 is shown as having a threaded portion for threaded engagement with an inner wall defining the passage 136. It should be understood that the stopper 135 may be releasably secured to and seal the passage 136 in any suitable manner.

Figure 14:
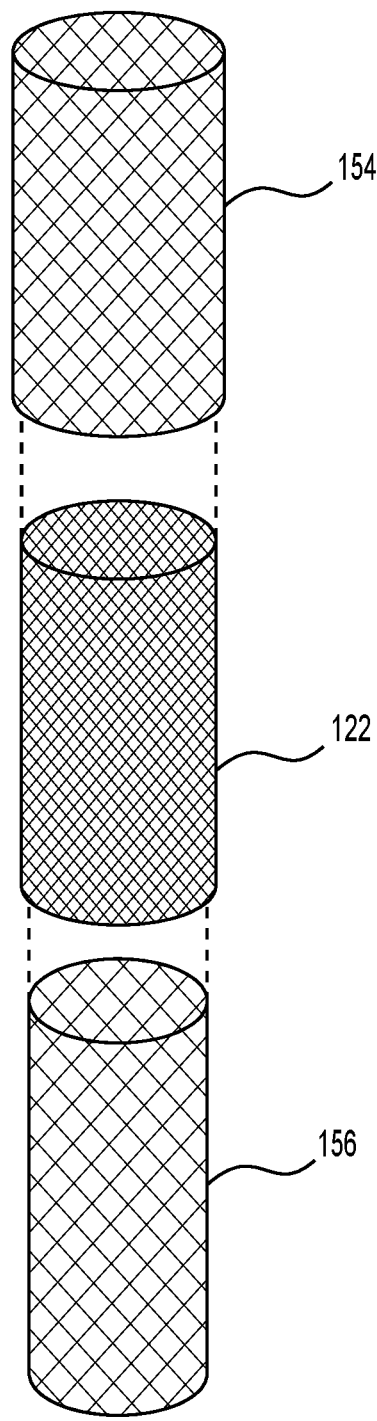
FIG. 14 is an exploded view of a cylindrical filter and mesh filter frame of the radial-flow membrane bioreactor of the embodiments of FIGS. 11 and 13.

Additionally, as illustrated in FIG. 14, a mesh cage may be provided for protecting and supporting the cylindrical filter 122. The cylindrical filter 122, or semipermeable membrane, is sandwiched between an inner mesh cylinder 156 and an outer mesh cylinder 154. The outer and inner mesh cylinders 154, 156 may be woven stainless-steel wire meshes attached to the lower and upper discs 112, 114 by epoxy adhesive glue or the like, and further sealed with silicone to eliminate any possibility of leakage from the reaction region R. Further, the lower and upper discs 112, 114 may each be provided with circular grooves, allowing the opposed circular edges of the cylindrical filter 122 and its mesh cage to be secured within the respective circular grooves.

It should be understood that the relative dimensions of the radial-flow membrane bioreactor 100 are shown for exemplary purposes only and may vary, depending upon the nature of the particular reactants and the desired reaction and production rate. For example, the cylindrical filter 122, which defines the reaction region R, may have an inner diameter of 10 cm and a height of 19 cm. Corresponding to these exemplary dimensions, the cylindrical sidewall 116 of hollow housing 111 may have an inner diameter of 24 cm. The combined base 130 and cylindrical sidewall 116 may have a height of 24 cm (i.e., the base 130 may have a thickness of 5 cm).

In the experiments, date seeds were used as the source of biological cellulose. After removal of extractives, characterization of fresh date seeds revealed concentrations of 47±0.7% cellulose, 28±0.4% hemicellulose, and 25±0.6% lignin. Alkaline pretreatment was used to remove lignin from the date seeds. To confirm the lignin content and to investigate the efficiency of lignin removal pretreatment, Klason lignin and acid-soluble lignin were quantified. Klason lignin and acid-soluble lignin in the fresh untreated date seeds were determined to be 24.01±2.47% and 0.16±5.59×$10^{-5}$%, respectively. The determined total lignin of 24.17% was in agreement with that found by the constituents' analysis. Klason lignin and acid-soluble lignin in the lignin-removed samples were found to be 16.6±2.6% and 3.95×$10^{-4}$±1.8×$10^{-4}$%, respectively. Thus, over 30% of total lignin was removed, which confirms the effectiveness of the alkaline pretreatment.

By using alkaline treatment at 4% NaOH for 1 hour at room temperature, 15.68% of lignin content was removed from date seeds. Operating at a higher temperature of 80° C. and 2% NaOH, a higher lignin removal of 70% was achieved from herbaceous lignocellulose, such as wheat straw, corn straw, and sugar bagasse. However, the increase in temperature was less effective with hardwood and softwood biomass, achieving a removal of 39.6% and 16%, respectively.

For the experiments, date seeds from Allig dates were obtained from the Liwa Company of Abu Dhabi, United Arab Emirates. The date seeds were washed with distilled water and then sun-dried and ground. The dried, ground date seeds were screened, and those with a size of 180 μm were used. "Extractives" are components that naturally exist in, or are attached to, biomass. To avoid interference of the free extractives in the pretreatment and enzymatic hydrolysis processes, and for an unbiased evaluation of the radial-flow membrane bioreactor 100, free extractives were removed in a Soxhlet extraction unit using ethanol for 8 hours. To characterize the substrate, the acid—base isolation method was used to quantify the three main constituents: cellulose, hemicellulose and lignin. Briefly, 10 g of substrate was mixed with 200 mL of 0.1 M HCl while being heated at 100° C. for 2 hours with stirring at 150 rpm. The mixture was vacuum-filtered to separate residues containing cellulose and lignin from the liquid containing hemicellulose. The residues were then washed with 20 mL of distilled water to remove any remaining hemicellulose left, followed by air drying overnight. The dried residues were then treated with 200 mL of 0.1 M NaOH for 2 hours at 100° C. under stirring at 150 rpm. Subsequently, the mixture was vacuum-filtered to separate residues containing cellulose from the lignin that was solubilized in NaOH. The residues were further washed with 20 mL of 0.1 M of NaOH and air-dried.

Figure 15:
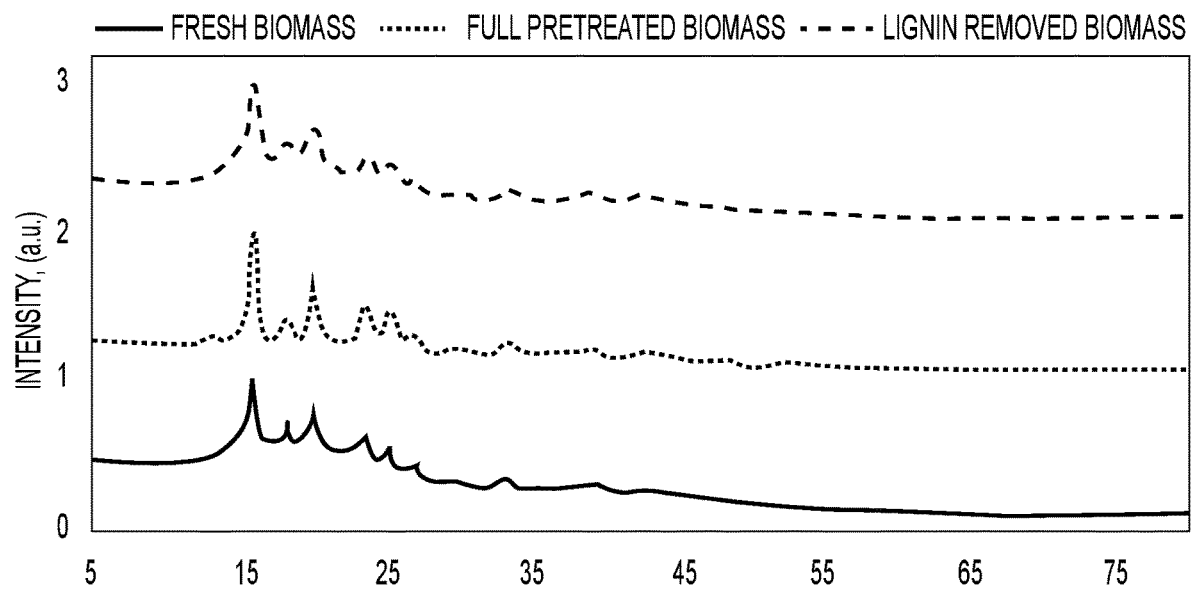
FIG. 15 is a composite X-ray diffraction (XRD) diffractogram comparing the XRD spectra of fresh date seed biomass against fully pretreated date seed biomass, and date seed biomass pretreated to remove lignin.

The effects of the full pretreatment and lignin removal treatment on the crystallinity of the date seeds were examined with X-ray diffraction (XRD), as shown in FIG. 15. The analysis showed a slight increase in the intensity after both treatments, which indicates an increase in the crystallinity. The peaks at 16° and 23° reflect crystalline cellulose type I, while cellulose type II is presented at 20°. The intensity of those peaks increased in both full-pretreatment and lignin-removed date seed biomass, which indicates a higher crystallinity degree in the structure of the treated fibers due to the removal of lignin. A similar increase in the intensity of peaks that represent crystalline cellulose was also observed with date seeds from *Phoenix dactylifera L.* after lignin and hemicellulose removal. It can also be seen that the increase in peak intensity with full pretreatment (i.e., removing both lignin and hemicellulose) was higher than that with lignin removal only. This suggests that the acid used in the full pretreatment may not have hydrolyzed hemicellulose only, but also the amorphous parts of the cellulose structure, resulting in increased crystallinity. As a result, the peaks at 25° and 26°, which reflect cellulose crystallinity and crystalline carbon, respectively, appeared only in the fully pretreated sample.

The XRD scans for measuring changes in the crystallography of the fresh, full-pretreated and lignin-removed date seed biomasses were performed with a 2θ range of 4-90°, a step size of 0.02°/s, a voltage of 40 kV, an intensity of 20 A, and Cu Kα radiation of 1.5406 Å.

Figure 16:
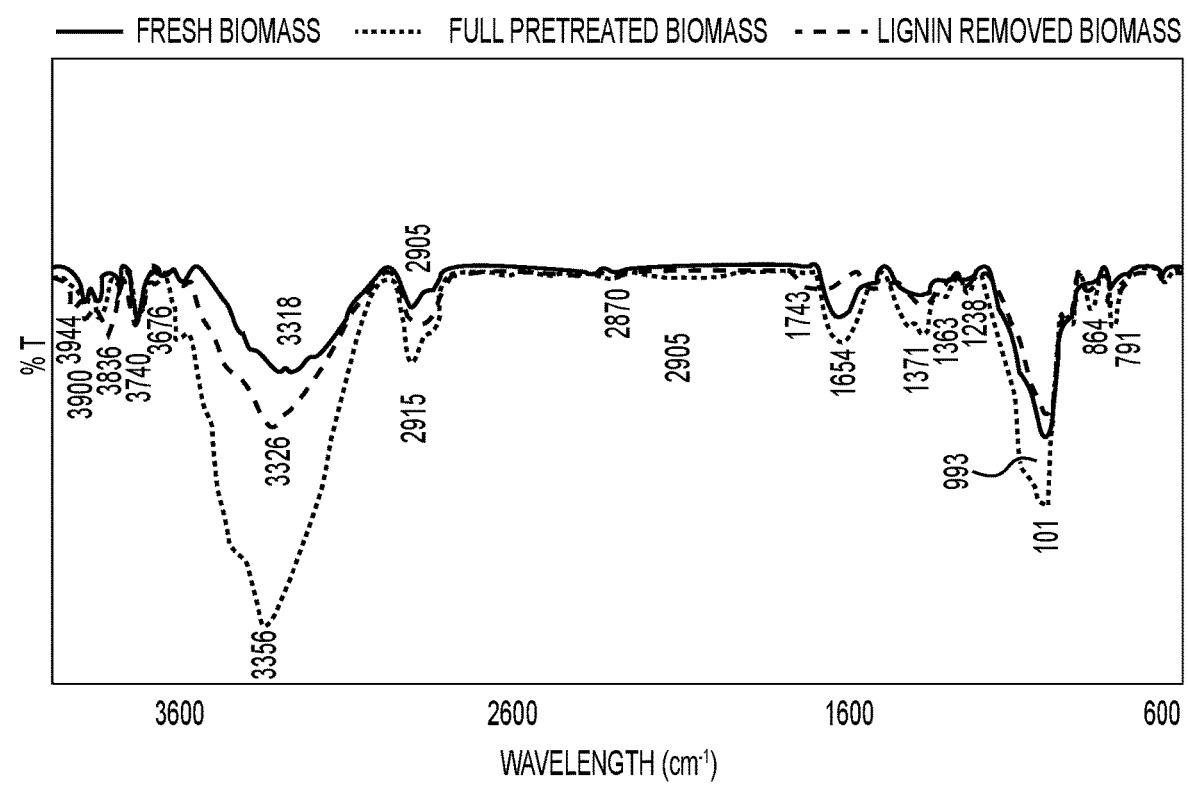
FIG. 16 are Fourier-transform infrared (FTIR) spectra of fresh date seed biomass compared against fully pretreated date seed biomass and date seed biomass pretreated to remove lignin.

Fourier transform infrared (FTIR) analysis was carried out to investigate the effect of full and lignin-removing pretreatments on the composition and functional groups in date seeds. FIG. 16 shows the FTIR spectra of fresh date seeds, full-pretreated date seeds, and lignin-removed date seeds. The peaks between 4000 and 2995 $cm^{-1}$ are assigned to hydrogen-bonded —OH stretching vibrations. Peaks at 2905 and 2855 $cm^{-1}$ are assigned to asymmetric and symmetric C—H stretching in methyl and methylene groups, respectively, and the peak at 2870 $cm^{-1}$ represents aliphatic CH stretching, to which all three main constituents, cellulose, hemicellulose, and lignin, contribute. The peak at 1654 $cm^{-1}$ reflects the C=C or C=N vibration in the aromatic region, which is influenced by the lignin. The band at 993 $cm^{-1}$ represents the C—O—C glycosidic bond vibration, and C—C stretching is assigned to the peak at 791 $cm^{-1}$, which are related to the cellulose component. After partial pretreatment, where lignin is removed, a similar spectrum to that of the fresh date seeds was observed, but with the appearance of two peaks at 1743 and 864 $cm^{-1}$. The former is assigned to the C=O bond that can be due to either the acetyl or the ester group found in hemicellulose, while the latter represents the C—H rocking vibration of cellulose. The appearance of those two peaks are signs of structural distribution and that lignin removal allowed the exposure of both cellulose and hemicellulose. By comparing the spectra of the full-pretreated date seeds, it was observed that peaks at 1371 and 1338 $cm^{-1}$ appeared, which are assigned to —CH stretching of cellulose, which indicates the biomass structural deformation after hemicellulose and lignin removal. The appearance of the band at 1238 $cm^{-1}$ can represent either C—O—H deformation or C—O phenolic stretching that might reflect traces of lignin found in the biomass. The appearance of a band at 864 $cm^{-1}$ represents, as noted above, the C—H rocking vibration of cellulose.

To analyze the functional groups in the fresh, full-pretreated and lignin-removed date seed biomasses, a Shimadzu® IRTracer-100 FTIR spectrophotometer was used. The FTIR spectra were recorded on an attenuated total reflection Fourier-transform infrared (ATR-FTIR) spectrograph using a range of 600-4000 $cm^{-1}$ with an average of 34 scans and a spectral resolution of 4 $cm^{-1}$.

Figure 17A:
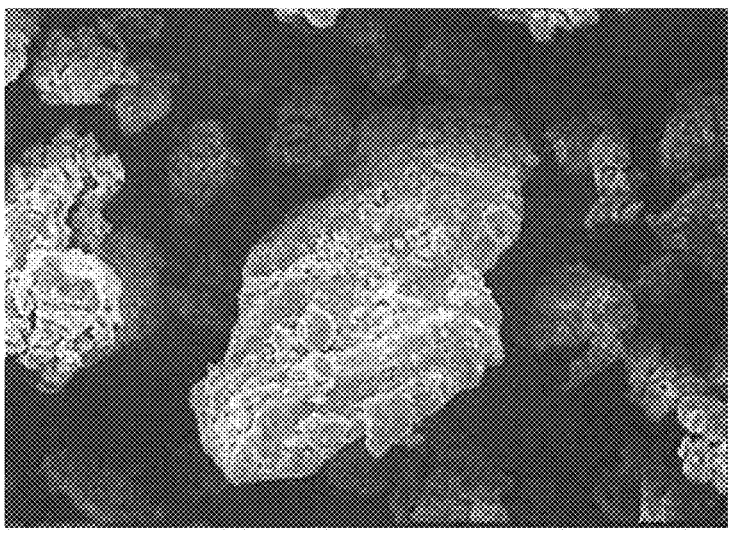
FIG. 17A is a SEM photomicrograph of the fresh date seed biomass of FIGS. 15 and 16.
Figure 17B:
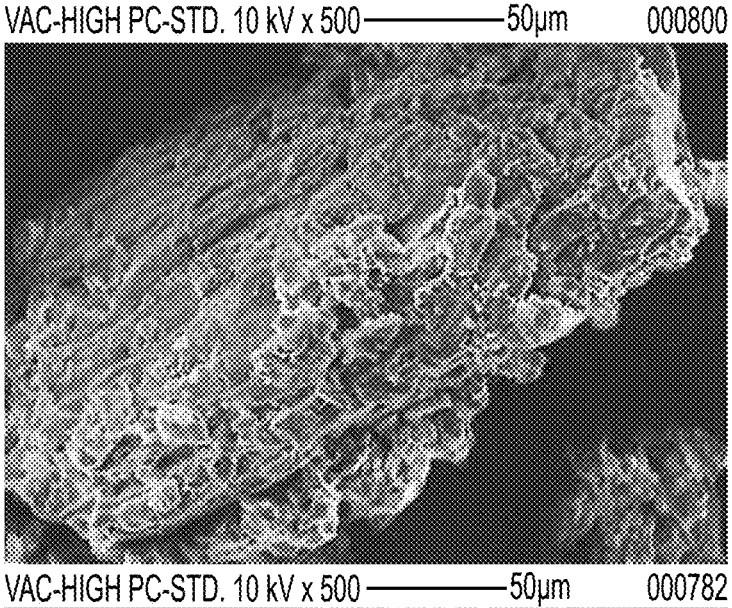
FIG. 17B is a SEM photomicrograph of the fully pretreated date seed biomass of FIGS. 15 and 16.
Figure 17C:
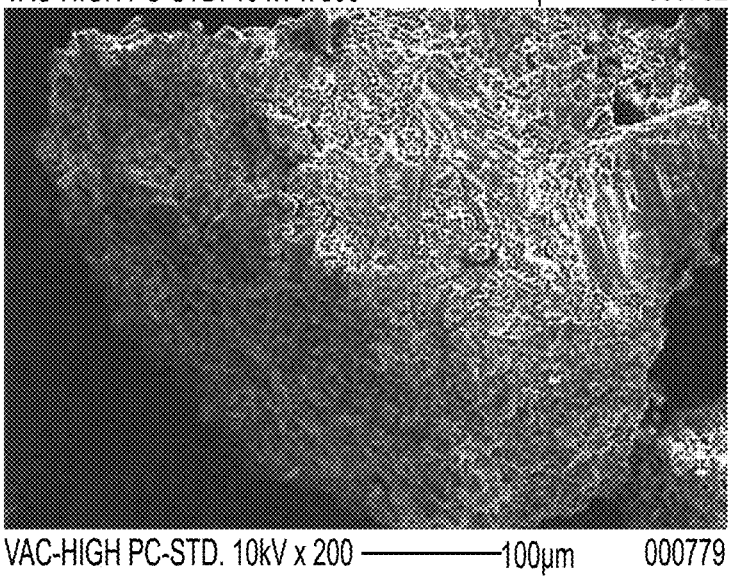
FIG. 17C is a SEM photomicrograph of the date seed biomass pretreated to remove lignin of FIGS. 15 and 16.

Scanning electron microscopy (SEM) was used to analyze the morphological changes as a result of full pretreatment and lignin removal pretreatment, as shown in FIGS. 17A-17C. The fresh date seed biomass, shown in FIG. 17A, was characterized by a smooth and solid surface. The effect of full pretreatment, including acid and NaOH treatment, is shown in FIG. 17B. It can be seen that the structure was disrupted due to the action of NaOH, leaving holes that can be observed on the surface of the molecules, while elongated, structural cracks indicate the severe action of acid treatment, attributed to the partial hydrolysis of the amorphous part of the biomass. Images of the lignin-removed date seed biomass, treated with only NaOH, are shown in FIG. 17C. It can be seen that the structure contained holes that indicate the disruption of the matrix due to lignin removal. However, unlike with the full-treated samples, with lignin removal only, the samples maintained a similar overall structure, without cracks.

The changes in the structural morphology due to the removal of lignin were detected using a Jeol® JCM-5000 NeoScope SEM. Fresh, full-pretreated, and lignin-removed date seed biomasses were coated with gold using a Jeol® JFC-1600 Auto Fine Coater to increase the conductivity of the non-conductive catalyst and to prevent the build-up of electrostatic charge at the specimen surface. The samples were inserted into the scanning electron microscope for observation.

Acid-based pretreatment was used to remove both hemicellulose and lignin to disrupt the lignocellulose structure and enhance the enzyme accessibility to cellulose. A preliminary test was performed to evaluate the need for the hemicellulose-removing step. The glucose yield from enzymatic hydrolysis of date seeds pretreated by the removal of lignin and hemicellulose was found to be close to that obtained using date seeds treated with lignin removal only. With complete pretreatment, the glucose yield after 8 hours of hydrolysis was 3.2%. Under the same conditions, the yield obtained from date seeds with lignin removal only was 3.5%. Similar reults were also observed when comparing the hydrolysis yield of corn stalk biomass fully pretreated by lignin and hemicellulose removal and partially pretreated by lignin removal only. After 96 hours of hydrolysis, the cellulose conversion in the fully pretreated samples was 70.3%, whereas it reached 100% in partially pretreated samples. Delignification only of loblolly pine biomass was also shown to increase the cellulose hydrolysis conversion after 72 hours by 88% as compared to untreated samples, where cellulose conversion was only 16%. The lower conversion of the fully pretreated samples is attributed to the use of acid, which, in addition to removing hemicellulose, dissolves some of the amorphous portion of cellulose. This increases the percentage of the crystalline cellulose in the fully pretreated sample observed in the XRD analysis, which results in a drop in the conversion yield. Therefore, all subsequent experiments using the radial-flow membrane bioreactor were carried out using date seed samples partially pretreated with lignin removal only.

As discussed above, the hydrolysis of fully treated samples, in which both lignin and hemicellulose were removed, was compared to that of partially treated samples, in which only lignin was removed while keeping the hemicellulose. For the latter case, 10 g of the substrate sample was treated only with 200 mL of 0.1 M NaOH for 2 hours. The removal of hemicellulose did not result in any enhancement in hydrolysis, and a similar yield was obtained to that obtained using fresh date seed biomass, as discussed above. Thus, all substrates used in subsequent experiments were on partially treated (i.e., lignin-removed) date seeds.

For the experiments on the radial-flow membrane bioreactor 100, cellulase from Trichoderma reesei was purchased from Sigma-Aldrich®. The enzyme activity was measured to be 1800 units/g. The activity unit is defined as the concentration of glucose, in grams, produced within 1 hour from the filter paper at 37° C. and a pH of 5. Dinitrosalicylic acid (DNS), glucose (99.5% purity), Bradford reagent for protein detection, and all other chemicals were purchased from Merck®. Sodium acetate (99%) and acetic acid (99%) were used to prepare a 0.1 M acetate buffer (pH 5) for controlling the pH of the system. Hydrochloric acid (HCl) (37%) and sodium hydroxide (NaOH) were purchased from Sigma-Aldrich®. Microdyn® Nadir hydrophilic polyethersulfone (PES) ultrafiltration membranes (297×210 mm) with a 10 kDa MWCO and a thickness of 230 µm were obtained from Sterlitech®.

Figure 18:
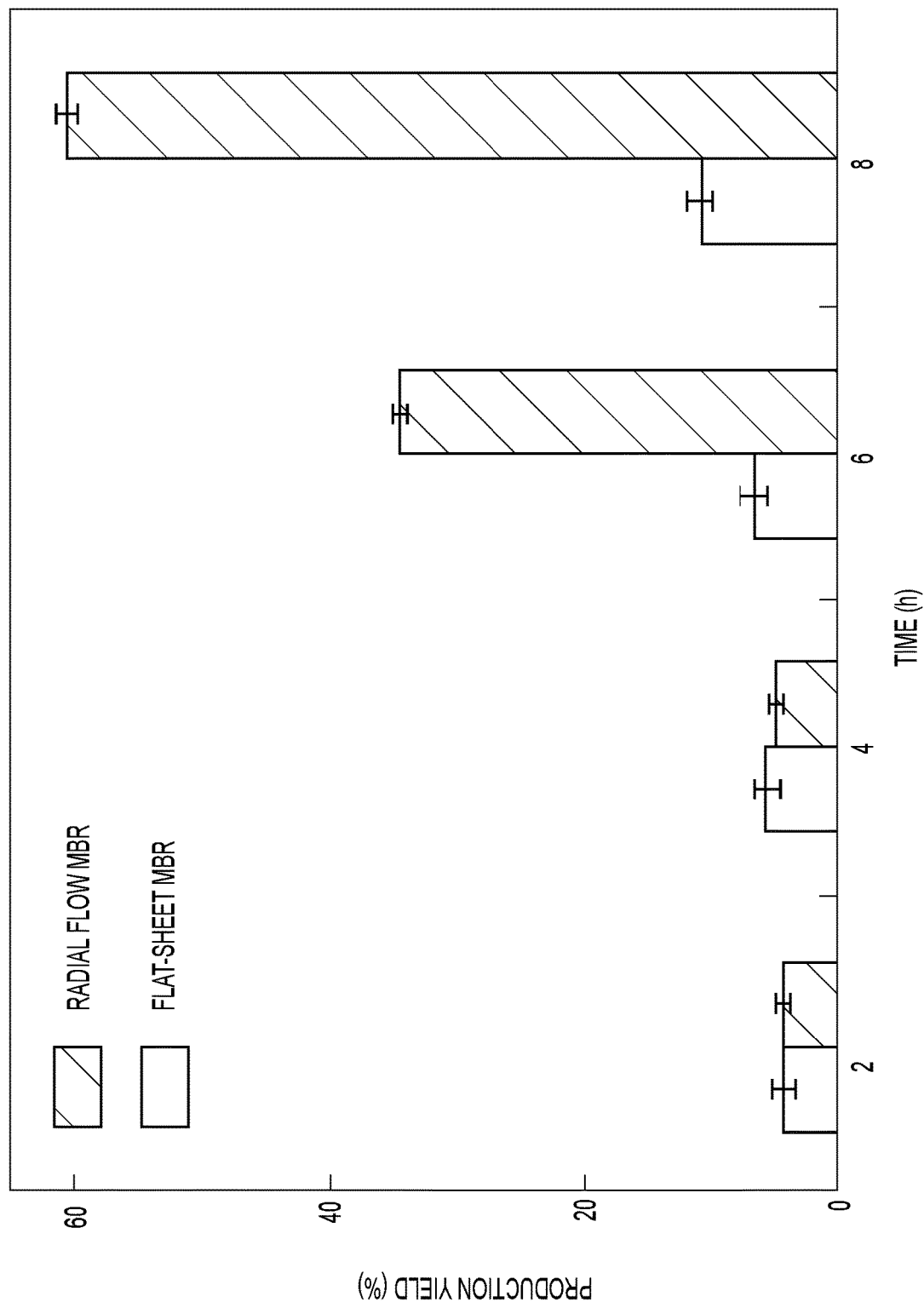
FIG. 18 is a plot comparing glucose production yield from the radial-flow membrane bioreactor against the membrane bioreactor for simultaneous enzymatic cellulose hydrolysis and product separation of FIG. 1.

FIG. 18 shows the glucose production yield from the enzymatic hydrolysis of partially treated date seeds using the radial-flow membrane bioreactor (MBR) 100, compared against the membrane bioreactor for simultaneous enzymatic cellulose hydrolysis and product separation 10 of FIG. 1 under the same conditions. As shown in FIG. 18, within 8 hours, the radial-flow membrane bioreactor 100 produced a glucose yield of approximately 60%. In the first 4 hours, the performance of both reactors was almost identical. This is because the concentration of the produced glucose was not high enough to cause inhibition. However, after 6 hours, the effect of glucose removal became more significant, and the enhanced yield of the radial-flow membrane bioreactor 100 over bioreactor 10 became more evident. The enhancement in the yield in the the radial-flow membrane bioreactor 100 is attributed to the increase in the diffusion area of the cylindrical membrane. The cylindrical membrane 122 surrounding the reaction region R throughout the bioreactor 100 facilitated more product separation and pushed the reaction in the forward direction when compared to the limited diffusion area provided in bioreactor 10. Additionally, at the substrate concentration used for the experiments, no mixing problems were encountered, which suggests that the bioreactor 100 can handle higher concentrations. In the comparison shown in FIG. 18, for both bioreactors, the substrate and enzyme concentrations were 13.3 g/L and 252 FPU/mL, respectively, at pH 5 and 48° C., with a water flux of 0.8 mL/min. An agitation speed of 450 rpm was used, and all experiments were conducted in triplicate.

In the above, glucose concentration was measured using the DNS method, which measures the total amount of reducing sugars in a sample. In this method, 45 µL of the sample was mixed with 40 µL of the DNS reagent and diluted with 315 µL of distilled water to reach a total volume of 400 µL. Then, the mixture was incubated at 100° C. for 5 minutes. To stop the reaction with DNS, the sample was incubated in ice for 10 minutes. The glucose was then quantified using a SPECTROstar® ultraviolet (UV) spectrophotometer manufactured by BMG Labtech® at 540 nm. The glucose concentration in the sample was determined by comparing the measured optical density against a calibration curve constructed using serial dilutions of a glucose solution of known concentration.

Protein measurement was performed using the Bradford reagent, which is an acidic Coomassie blue dye that binds stably to proteins. The protein concentration was quantified by measuring the optical density at 595 nm and compared to a calibration curve constructed using serial dilutions of a cellulase solution of known concentration.

The lignin content of fresh and lignin-removed date seed samples was determined in accordance with the NREL LAP-003 protocol. In this protocol, both acid-insoluble lignin, known as Klason lignin, and acid-soluble lignin were quantified. Briefly, 0.3 g of the extractive-free sample was treated with 72% sulfuric acid ($H_2SO_4$) at 30° C. for 2 hours with mixing every 15 minutes. The solution was then diluted with 84 mL of distilled water to reach a 4% acid concentration, after which it was autoclaved for 1 hour at 121° C. The sample was then allowed to cool down before being vacuum-filtered to separate the liquid from the residues. The residual part, which contained the Klason lignin, was placed in a muffle furnace at 575° C. for 3 hours to determine the ash content. The acid-soluble lignin was determined by measuring the absorbance of the liquid filtrate at 205 nm.

It is to be understood that the membrane bioreactor for simultaneous enzymatic cellulose hydrolysis and product separation is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A radial-flow membrane bioreactor for enzymatic cellulose hydrolysis and product separation, comprising:
a hollow housing having a lower wall, an upper wall and a cylindrical sidewall, the cylindrical sidewall having an outlet port mounted thereon, the upper wall having an inlet port mounted thereon; and
a cylindrical filter mounted coaxially within the hollow housing and extending between the lower wall and the upper wall, the cylindrical filter being a semipermeable polyethersulfone membrane permeable to glucose and impermeable to enzymes hydrolyzing cellulose, the cylindrical filter defining an inner cylindrical reaction region inside the cylindrical filter and an outer cylindrical annulus product collection region between the cylindrical filter and the cylindrical sidewall of the housing; the inlet port extending into the reaction region and being adapted for introducing water, cellulose, and an enzyme hydrolyzing cellulose into the reaction region, the outlet port being adapted for continuously removing an aqueous solution of glucose hydrolyzed from the cellulose from the outer cylindrical annulus product collection region after flowing radially through the cylindrical filter.

2. The radial-flow membrane bioreactor as recited in claim 1, further comprising means for stirring the reaction region.

3. The radial-flow membrane bioreactor as recited in claim 2, wherein the means for stirring the reaction region comprises a magnetic stirrer.

4. The radial-flow membrane bioreactor as recited in claim 1, further comprising a hot plate, the bioreactor being placed on the hot plate for heating the reaction region.

5. The radial-flow membrane bioreactor as recited in claim 1, wherein the upper wall of the hollow housing comprises an upper disc releasably sealed to an inner surface of the cylindrical sidewall.

6. The radial-flow membrane bioreactor as recited in claim 5, wherein the lower wall of the hollow housing comprises a lower disc releasably sealed to the inner surface of the cylindrical sidewall.

7. The radial-flow membrane bioreactor as recited in claim 6, further comprising a base having a recess formed therein, the hollow housing being mounted on the base such that the lower disc is releasably received within the recess.

8. The radial-flow membrane bioreactor as recited in claim 7, further comprising at least one support extending between the upper disc and the lower disc.

9. The radial-flow membrane bioreactor as recited in claim 8, wherein the upper disc has a passage defined therein, the bioreactor further comprising a stopper removably seated in and sealing the passage, the inlet port extending through the stopper.

10. The radial-flow membrane bioreactor as recited in claim 9, further comprising a conduit extending through the inlet port from an exterior of the stopper into the reaction region.

11. The radial-flow membrane bioreactor as recited in claim 1, further comprising an insulating jacket removably wrapped around the hollow housing.

12. The radial-flow membrane bioreactor as recited in claim 1, further comprising a mesh cage supporting the cylindrical filter.

13. A radial-flow membrane bioreactor for enzymatic cellulose hydrolysis and product separation, comprising:
a hollow housing having a lower wall, an upper wall and a cylindrical sidewall, the cylindrical sidewall having an outlet port mounted therein, and the upper wall having an inlet port mounted therein;
a cylindrical filter mounted coaxially within the hollow housing and extending between the lower wall and the upper wall, the cylindrical filter including a semipermeable polyethersulfone membrane permeable to glucose and impermeable to cellulase enzymes, the cylindrical filter defining an inner reaction region extending inside the cylindrical filter between the upper wall and the lower wall of the housing and an outer cylindrical annulus extending between the cylindrical filter and the cylindrical sidewall of the housing and between the upper and lower walls of the housing; and
a conduit extending through the inlet port from an exterior of the hollow housing into the reaction region, the conduit being adapted for delivering water and cellulase into the reaction region for hydrolyzing cellulose to produce glucose in aqueous solution, the aqueous glucose product continuously flowing radially outward into the cylindrical annulus product collection region and removed from the bioreactor through the outlet port.

14. The radial-flow membrane bioreactor as recited in claim 13, further comprising means for stirring the reaction region.

15. The radial-flow membrane bioreactor as recited in claim 14, wherein the means for stirring the reaction region comprises a magnetic stirrer.

16. The radial-flow membrane bioreactor as recited in claim 13, further comprising a hot plate, the bioreactor being placed on the hot plate for heating the reaction region.

17. The radial-flow membrane bioreactor as recited in claim 13, wherein the upper wall of the hollow housing comprises an upper disc releasably sealed to an inner surface of the cylindrical sidewall.

18. The radial-flow membrane bioreactor as recited in claim 17, wherein the lower wall of the hollow housing comprises a lower disc releasably sealed to the inner surface of the cylindrical sidewall.

19. The radial-flow membrane bioreactor as recited in claim 18, further comprising a base having a recess formed therein, the hollow housing being mounted on the base such that the lower disc is releasably supported within the recess.

20. The radial-flow membrane bioreactor as recited in claim 13, further comprising:
- at least one support extending between the upper disc and the lower disc; and
- a stopper removably seated within a passage formed in the upper disc, the inlet port being formed through the stopper.

* * * * *